US012622963B2

(12) United States Patent
Jaklenec et al.

(10) Patent No.:    US 12,622,963 B2
(45) Date of Patent:    *May 12, 2026

(54) MICROMOLDED OR 3-D PRINTED PULSATILE RELEASE VACCINE FORMULATIONS

(71) Applicants:Massachusetts Institute of Technology, Cambridge, MA (US); Tokitae LLC, Bellevue, WA (US)

(72) Inventors: Ana Jaklenec, Lexington, MA (US); William Gates, Redmond, WA (US); Philip A. Welkhoff, Kirkland, WA (US); Boris Nikolic, Seattle, WA (US); Lowell L. Wood, Jr., Bellevue, WA (US); Robert S. Langer, Newton, MA (US); Thanh Duc Nguyen, Manchester, CT (US); Stephany Yi Tzeng, Somerville, MA (US); James J. Norman, Rockville, MD (US); Kevin McHugh, Houston, TX (US)

(73) Assignees: Massachusetts Institute of Technology, Cambridge, MA (US); Tokitae LLC, Bellevue, WA (US)

( * ) Notice:    Subject to any disclaimer, the term of this patent is extended or adjusted under 35 U.S.C. 154(b) by 0 days.

This patent is subject to a terminal disclaimer.

(21) Appl. No.: 18/400,533

(22) Filed:    Dec. 29, 2023

(65)    Prior Publication Data

US 2024/0181047 A1     Jun. 6, 2024

Related U.S. Application Data

(60) Continuation of application No. 17/143,871, filed on Jan. 7, 2021, now Pat. No. 11,975,069, which is a division of application No. 16/401,476, filed on May 2, 2019, now Pat. No. 10,960,073, which is a division of application No. 14/572,631, filed on Dec. 16, 2014, now Pat. No. 10,300,136.

(60) Provisional application No. 61/916,555, filed on Dec. 16, 2013.

(51) Int. Cl.
*A61K 39/39*      (2006.01)
*A61K 39/00*      (2006.01)
*A61K 39/12*      (2006.01)

(52) U.S. Cl.
CPC .............. *A61K 39/39* (2013.01); *A61K 39/00* (2013.01); *A61K 39/12* (2013.01); *A61K 2039/545* (2013.01); *A61K 2039/55555* (2013.01); *A61K 2039/55566* (2013.01); *A61K 2039/6093* (2013.01); *C12N 2770/32634* (2013.01); *Y02A 50/30* (2018.01)

(58) Field of Classification Search
None
See application file for complete search history.

(56)    References Cited

U.S. PATENT DOCUMENTS

| | | | |
|---|---|---|---|
| 4,450,150 | A | 5/1984 | Sidman |
| 5,490,962 | A | 2/1996 | Cima |
| 6,312,731 | B1 | 11/2001 | Staas |
| 6,565,532 | B1 | 5/2003 | Yuzhakov |
| 8,545,830 | B2 | 10/2013 | Lowe et al. |
| 9,040,090 | B2 | 5/2015 | Desimone |
| 9,045,728 | B2 | 6/2015 | Coffey |
| 10,300,136 | B2 | 5/2019 | Jaklenec |
| 10,384,372 | B2 | 8/2019 | Vecchione |
| 10,478,398 | B2 | 11/2019 | Park |
| 10,960,073 | B2 | 3/2021 | Jaklenec |
| 11,975,069 | B2 * | 5/2024 | Jaklenec ................. A61P 31/04 |
| 12,390,537 | B2 | 8/2025 | Langer et al. |
| 2002/0107470 | A1 | 8/2002 | Richards |
| 2004/0022840 | A1 | 2/2004 | Nagy |

(Continued)

FOREIGN PATENT DOCUMENTS

| | | |
|---|---|---|
| AU | 2015095230 | 6/2015 |
| AU | 2014364930 | 7/2016 |

(Continued)

OTHER PUBLICATIONS

Alcock, et al., "Long-term thermostabilization of live poxviral and adenoviral vaccine vectors at supraphysiological temperatures in carbohydrate glass", Vaccines, 2(19):19ra12 (2010).
Amodwala, et al., "Statistically optimized fast dissolving microneedle transdermal patch of meloxicam: A patient friendly approach to manage arthritis", European Journal of Pharmaceutical Sciences, 104:114-123 (2017).
Antohe and Wallce, "Ink-jet as a manufacturing method for drug delivery applications", Proceedings of the 2008 Manfact Sci and Eng Conf., Oct. 7-10, Rvanston, Illinois (2008).
Arthanari, et al., "Preparation and evaluation of sucrose stabilized tetanus toxoid encapsulated into chitosan microspheres", Genomic Medicine, Biomarkers, and Health Sciences, 3:91-97 (2011).
Astete, et al., "Synthesis and characterization of PLGA nanoparticles", J Biomater Sci Polymer Edn., 17(3):247-89 (2006).

(Continued)

*Primary Examiner* — Benjamin P Blumel
(74) *Attorney, Agent, or Firm* — Pabst Patent Group LLP

(57)    ABSTRACT

Emulsion-based and micromolded ("MM") or three dimensional printed ("3DP") polymeric formulations for single injection of antigen, preferably releasing at two or more time periods, have been developed. Formulations are preferably formed of biocompatible, biodegradable polymers. Discrete regions encapsulating antigen, alone or in combination with other antigens, adjuvants, stabilizers, and release modifiers, are present in the formulations. Antigen is preferably present in excipient at the time of administration, or on the surface of the formulation, for immediate release, and incorporated within the formulation for release at ten to 45 days after initial release of antigen, optionally at ten to 90 day intervals for release of antigen in one or more additional time periods. Antigen may be stabilized through the use of stabilizing agents such as trehalose glass. In a preferred embodiment for immunization against polio, antigen is released at the time of administration, and two, four and six months thereafter.

9 Claims, 24 Drawing Sheets

(56) References Cited

U.S. PATENT DOCUMENTS

| | | | |
|---|---|---|---|
| 2004/0033241 | A1 | 2/2004 | Donovan |
| 2004/0166140 | A1 | 8/2004 | Santini et al. |
| 2004/0175410 | A1 | 9/2004 | Ashton et al. |
| 2004/0241236 | A1 | 12/2004 | Li |
| 2005/0050859 | A1 | 3/2005 | Coppeta et al. |
| 2007/0031505 | A1 | 2/2007 | Roy |
| 2007/0141106 | A1 | 6/2007 | Bonutti et al. |
| 2008/0026040 | A1 | 1/2008 | Farr |
| 2010/0278931 | A1 | 11/2010 | Ashton et al. |
| 2011/0129474 | A1 | 6/2011 | Shoemaker |
| 2012/0238994 | A1 | 9/2012 | Nazzaro et al. |
| 2013/0046182 | A1 | 2/2013 | Hegg |
| 2013/0202707 | A1 | 8/2013 | Ali et al. |
| 2013/0204233 | A1 | 8/2013 | Zou |
| 2014/0005606 | A1 | 1/2014 | Chen |
| 2014/0309610 | A1 | 10/2014 | Canham et al. |
| 2014/0336487 | A1 | 11/2014 | Wang et al. |
| 2015/0165020 | A1 | 6/2015 | Jaklenec |
| 2016/0120799 | A1 | 5/2016 | Chiang |
| 2016/0136406 | A1 | 5/2016 | Berry |
| 2017/0055499 | A1 | 3/2017 | Peppou |
| 2017/0157036 | A1 | 6/2017 | D'Souza |
| 2018/0296491 | A1 | 10/2018 | Delouise |
| 2019/0015650 | A1 | 1/2019 | Jaklenec et al. |
| 2019/0076631 | A1 | 3/2019 | Mchugh et al. |
| 2021/0290921 | A1 | 9/2021 | Mchugh et al. |
| 2021/0354984 | A1 | 11/2021 | Langer et al. |

FOREIGN PATENT DOCUMENTS

| | | |
|---|---|---|
| CA | 3082793 | 3/2019 |
| CN | 103251941 | 8/2013 |
| CN | 113350564 A | 9/2021 |
| EP | 3082852 | 10/2016 |
| JP | 2009504027 | 4/1997 |
| JP | 2009035557 | 2/2009 |
| JP | 2010180228 | 8/2010 |
| JP | 2011514337 | 5/2011 |
| JP | 2011155988 | 8/2011 |
| JP | 2012235899 A | 12/2012 |
| RU | 2508135 | 2/2014 |
| WO | 95011010 | 4/1995 |
| WO | 0126708 | 4/2001 |
| WO | 02064162 | 8/2002 |
| WO | 03092633 | 11/2003 |
| WO | 2005071088 | 8/2005 |
| WO | 2007001448 | 1/2007 |
| WO | 2007012114 | 2/2007 |
| WO | 2007027273 | 3/2007 |
| WO | 2009051837 | 4/2009 |
| WO | 2009108689 | 9/2009 |
| WO | 2011156641 | 12/2011 |
| WO | 2013181107 | 12/2013 |
| WO | 2014004301 | 1/2014 |
| WO | 2018119274 | 6/2018 |
| WO | 2021136933 | 7/2021 |

OTHER PUBLICATIONS

Audran, et al., "Encapsulation of peptides in biodegradable microspheres prolongs their MHC class-I presentation by dendritic cells and macrophages in vitro", Vaccine, 21(11-12):1250-1255 (2003).

Blikstein, et al., "Digital fabrication and Making in Education: The Democratization of Invention", Digital Fabrication, Sep. 18-21, 2005.

Boehm et al., "Modification of microneedles using inkjet printing", AIP Advances, 1:2, 022139 (2011).

Bohmer, et al., "Preparation of monodisperse polymer particles and capsules by ink-jet printing", Colloids Surfaces, 289:96-104 (2006).

Brambilla, et al., "Microneedles for the noninvasive structural and functional assessment of dermal lymphatic vessels", Small, 12(8):1053-1061 (2016).

Cleland, "Single-administration vaccines: controlled-release technology to mimic repeated immunizations", Trends Biotechnol., 17(1):25-9 (1999).

Cleland, et al.., "Development of a single-shot subunit vaccine for HIV-1:Part 4. Optimizing microencapsulation and pulsatile release of MN rgp120 from biodegradable microspheres", J Cont. Release, 47(2):135-50 (1997).

Cui, et al., "Thermal inkjet in tissue engineering and regenerative medicine", Recent Pat. Drug Del. Formul., 6(2):149-155 (2012).

Eldridge, et al., "Biodegradable microspheres as a vaccine delivery system", Molecular Immunology, 28(3):287-94 (1991).

Ermak and Giannasca, "Microparticle targeting to M cells", Adv Drug Delivery Rev., 34:261-83 (1998).

Gregory, et al., "Vaccine delivery using nanoparticles", Frontiers Cellular Infection Microbiol., 3(13):1-13 (2013).

Hanes, et al., "New advances in microsphere-based single-dose vaccines", Adv. Drug. Del. Rev., 28 97-119 (1997).

Huang, et al., "Levofloxacin implants with predefined microstrucutre fabricated by three-dimensional printing technique", Int. J. of Pharm., 339:33-38 (2007).

International Search Report and Written Opinion for PCT/US2014/070664 mailed Mar. 20, 2015.

International Search Report for PCT application PCT/US2018/050822, mailed Jan. 18, 2019.

International Search Report for PCT/US2018/0412322 dated Nov. 7, 2018.

International Search Report for PCT/US2021/031675 dated Sep. 15, 2021.

Jaklenec, et al., "Sequential release of bioactive IGF-I and TGF-beta 1 from PLGA microsphere-based scaffolds", Biomaterials, 29(10):1518-25 (2007).

Jang, et al., "Influence of fluid physical properties on ink-jet printability", Langmuir, 25:2629-2635 (2009).

Johansen, et al., "Improving Stability and Release Kinetics of Microencapsulated Tetanus Toxoid by Co-Encapsulation of Additives", Pharmaceutical Research, 15(7):1103-1110 (1998).

Junkins, et al., "A robust microparticle platform for a STING-targeted adjuvant that enhances both humoral and cellular immunity during vaccination", J. Control. Release, 270:1-13 (2018).

Khademhosseini, et al., "Microscale technologies for tissue engineering and biology", PNAS, 103(8):2480-7 (2006).

Kim, et al., "Microspheres for Drug Delivery", BioMEMS and Biomed Nanotechn, 1:19-50 (2006).

Kirby, et al., "Formulation and characterization of PLGA microspheres as vaccine adjuvants", Immunomic Discovery of Adjuvants and Candidate Subunit Vaccines, 13:263-289 (2013).

Kraan, et al., "Development of thermostable lyophilized inactivated polio vaccine", Pharm Res., 31:2618-29 (2014).

Lan, "Design and Fabrication of a Modular Multi-Material 3D Printer", M.Sc. Thesis: Massachusetts Institute of Technology, 2013; and at web site imagexpert.com/site-new/pdf/IXjetXpert.pdf. (2013).

Lelux, et al., "Micro and nanoparticle-based delivery systems for vaccine immunology: an immunological and materials perspective", Adv. Healthcare Mater., 2:72-94 (2013).

Li, et al., "A robust true direct-print technology for tissue engineering", Proceedings of the 2007 Intl. Manufat. Sci. and Eng. Conf., Oct. 15-17, Atlanta Georgia (2007).

Liu, et al., "Glass Transition Temperature of PLGA Particles and the Influence on Drug Delivery Applications", Polymers, 14:993 (2022).

Liu, et al., "Application and performance of 3D printing in nanobiomaterials", J Nanomaterials, 2013:681050 (2013).

Murillo, et al., "Influence of the co-encapsulation of different excipients on the properties of polyester microparticle-based vaccine against brucellosis", International Journal of Pharmaceutics, 271(1-2):125-135 (2004).

Nandedkar, "Nanovaccines: recent developments in vaccination", J Biosci, 34(6):995-1003 (2009).

Nuxoll, "BioMEMS in drug delivery", Adv Drug Deliv Rev., 65(11):1611-25 (2013).

Ogra, et al., "Vaccination strategies for mucosal immune responses", Clinic Microbiol Rev., 14(2):430-45 (2001).

(56)                References Cited

OTHER PUBLICATIONS

Park, et al., "Polymer particle-based micromolding to fabricate novel microstructures", Biomed. Microdevices, 9(2):223-234 (2007).

Quintanar-Guerrero, et al., "Preparation techniques and mechanisms of formation of biodegradable nanoparticles from performed polymers", Drug Dev Indust Pharm., 24(12):1113-28 (1998).

Radelescu, et al., "3D Printing of biological materials for drug delivery and tissue engineering applications", Digital Fabrication, 1:96-99 (2005).

Sanchez, et al., "Pulsed controlled-released system for potential use in vaccine delivery", J Pharm Sci., 85(6):547-52 (1996).

Takada, et al., "Soluble micro needle array tip for delivering e.g. ophthalmic diagnostic fluorescein into human skin, performs attachments of skin on substrate, where target substance eluted from array is absorbed through perforation", Database WPI section Ch, week 201281 Thomson Scientific, London, GB, Class A96, AN 2012-Q82066,XP002785753 (2017).

Tekin, et al., "Inkjet printing as a deposition and patterning tool for polymers and inorganic particles", Soft Matter, 4:703-13 (2008).

Vila, et al., "Design of biodegradable particles for protein delivery", J Cont. Rel., 78:15-24 (2002).

Xu, et al., "pH-responsive polymeric particulate systems for micronutrients fortification of salt", Biomedical Engineering Society, presented Oct. 23, 2018, Salt Lake City, Utah.

Lee, Byung Kook, et al., "Fabrication of drug-loaded polymer microparticles with arbitrary geometries using piezoelectric inkjet printing system." International journal of pharmaceutics 427. 2(2012):305-310(2012).

Ramazani, Farshad, et al., "Strategies for encapsulation of small hydrophillic and amphiphillic drugs inPLGA microspheres: state-of-the-art and challenges." International journal of pharmaceutics 499.1-2(2016) 358-367(2016).

McHugh, et al., "Fabrication of fillable microparticles and other complex 3D microstructures", Science, 357(6356):1138-1142 (2017).

Anothe, et al., "Ink-jet as a manufacturing method for drug delivery applications", Proceedings of the 2008 Manufact. Sci. and Eng. Conf. (2008).

Cui, et al. "Thermal inkjet in tissue engineering and regenerative medicine" Recent Pat Drug Deliv Fourmul., 6(2):149-55 (2012).

Kim and Pack, "Microspheres for drug delivery", BioMEMS and Biomedical Nanotechnology, Eds Ferrari, A.P. Lee, J. Lee, pp. 19-50 (2006).

Kirby, et al., "Formulation and characterization of PLGA microspheres as vaccine adjuvants", Immunomic Discovery of Adjuvants and Candidate Subunit Vaccines, Editors: Darren R. Flower and Yvonne Perrie, Chapter 13 pp. 263-289 (2013).

Lelux and Roy, "Micro and nanoparticle-based delivery systems for vaccine immunology: an immunological and materials perspective", Adv healthcare Mater., 2:72-94 (2013).

Li, et al., "A robust true direct-print technology for tissue engineering", Proceedings of the 2007 Intl Manfact Sci and Eng Conf., Oct. 15-17, Atlanta Georgia (2007).

Liu, et al., "Application and performance of 3D printing in nanobiomaterials", J Nanomaterials, 2013:681050:1-7 (2013).

Ogra, et al., "Vaccination strategies for mucosal immune responses", Clinic Microbial Rev., 14(2):430-445 (2001).

Park, et al., "Polymer particle-based micromolding to fabricate novel microstructures", Biomed. Microdevices, 9:223-34 (2007).

Radulescu, et al. "3D printing of biological materials for drug delivery and tissue engineering applications", Digital Fabrication, vol. lISBN / ISSN: 0-89208-258-5:96-9 (2005).

Xu, et al "pH-responsive polymeric particulate systems for micronutrients fortification of salt", Biomedical Engineering Society, presented Oct. 23, Salt Lake City UT.

Langer, et al., "New advances in microsphere-based single-dose vaccines", Adv. Drug. Del. Rev., 28 97-119 (1997).

Radulecu, et al., "Digital fabrication and Making in Education: The Democratization of Invention", Digital Fabrication Sep. 18-21, 2005.

Astete, et al., "Synthesis and characterization of PLGA nanoparticles", J Biomater Sci. Polymer Edn., 17(3)247-289 (2006).

Bohmer, et al., "Preparation of monodisperse polymer particles and capsules by ink-jet printing", Colloids and Surfaces A: Physiochem. Eng. Aspects, 289: 96-104 (2006).

Eldridge, et al., "Biodegradable microspheres as a vaccine delivery system", Molecular Immunology, 28(3):287-294 (1991).

Gregory, et al., "Vaccine delivery using nanoparticles", Frontiers in Cell and Infection Microbiology, 3:1-13 (2013).

Khademhosseini, et al., "Microscale technologies for tissue engineering and biology", PNAS, 103(8):2480-2487 (2006).

Nandedkar, "Nanovaccines: recent developments in vaccination", J. Biosci., 34:995-1003 (2009).

Nuxoll, et al., "BioMEMS in drug-delivery", Advanced Drug Delivery Reviews, 65(11):1611-1625 (2013).

Alcock, et al., "Long-term thermostabilization of live poxviral and adenoviral vaccine vectors at supraphysiological temperatures in carbohydrate glass", Vaccines, 2(19):19ra1 (2010).

Cleland, et al. "Single-administration vaccines: controlled-release technology to mimic repeated immunizations", Trends in Biotechnology, 17(1):25-29 (1999).

Cleland, et al., "Development of a single-shot subunit vaccine for HIV-1: Part 4. Optimizing microencapsulation and pulsatile release of MN rgp120 from biodegradable microspheres", J. Controlled Rel. 47(2):135-150 (1997).

Ermak, et al., Microparticle targeting to M cells, Adv. Drug Delivery Rev., 34:261-283 (1998).

Jaklenec, et al., "Sequential release of bioactive IGF-I and TGF-beta 1 from PLGA microsphere-based scaffolds", Biomaterials, 29(10:1518-1525 (2007).

Kraan, et al., "Development of thermostable lyophilized inactivated polio vaccine", Pharm. Res., 31:2618-2629 (2014).

Quintanar-Guerrer, et al., "Preparation techniques and mechanisms of formation of biodegradeable nanoparticles from performed polymers", Drug Dev. Indust. Pharm., 24(12):1113-1128 (1998).

Sanchez, et al., "Pulsed controlled-release system for potential use in vaccine delivery", Journal of Pharmaceutical Sciences, American Pharmaceutical Association, 85(6):547-552 (1996).

CASTEM , "CASTEM ultra-fine 3D modeling service", CASTEM Co., Ltd. Tokyo Branch. Available at <https://www.castem.co.jp/frontend/download/file/bisai_3d.pdf?epository=page&saved_as=d63a0ab0a637829a75a894a13701c618.pdf&name=bisai_3d.pdf>, Sep. 19, 2024, 2 pages (Japanese Copy Only).

Megahed , et al., "The Interactions Between HBV and the Innate Immunity of Hepatocytes", Viruses, vol. 12, No. 3: 285, Mar. 5, 2020, 14 pages.

* cited by examiner

Model protein release kinetics
PLLA – 50k

*Burst peaks:*
F28 – 0, 19, and 23 weeks, ...
F32 – 1 and 13 weeks, ...

Model protein release kinetics
PLLA – 100k

Burst peaks:
F29 – 0 weeks, ...
F33 – none, ...

Model protein release kinetics
PLLA – 300k

*Burst peaks:*
F30 – 0 and 13 weeks, ...
F34 – none, ...

Model protein release kinetics
P(d,l)LA – 20k

*Burst peaks:*
F31 – 0 and 13 weeks, ...
F35 – 3, 9, 12, and 17 weeks, ...

FIG. 7A                    FIG. 7B

Model protein release kinetics
PLGA-COOH - 50/50 – 20k, 0.5% Loading

*Burst peaks:*
F3 – 0, 3, and 6.5 weeks
F40 – 0, 2, and 6.5 weeks

Model protein release kinetics
PLGA-COOH - 50/50 – 31k, 5% Loading

*Burst peaks:*
F5 – 0, 3, and 8 weeks
F41 – 0, 3, 7, and 13 weeks

Model protein release kinetics
PLGA-COOH - 50/50 – 31k, 0.5% Loading

*Burst peaks:*
F7 – 0, 4, 8, and 11 weeks
F43 – 0, 3, 8 and 11 weeks

Emulsion method

Protein/drug

Biodegradable polymer (PLGA, PLA etc.)

3D printing

3D-printing Encapsulation Process
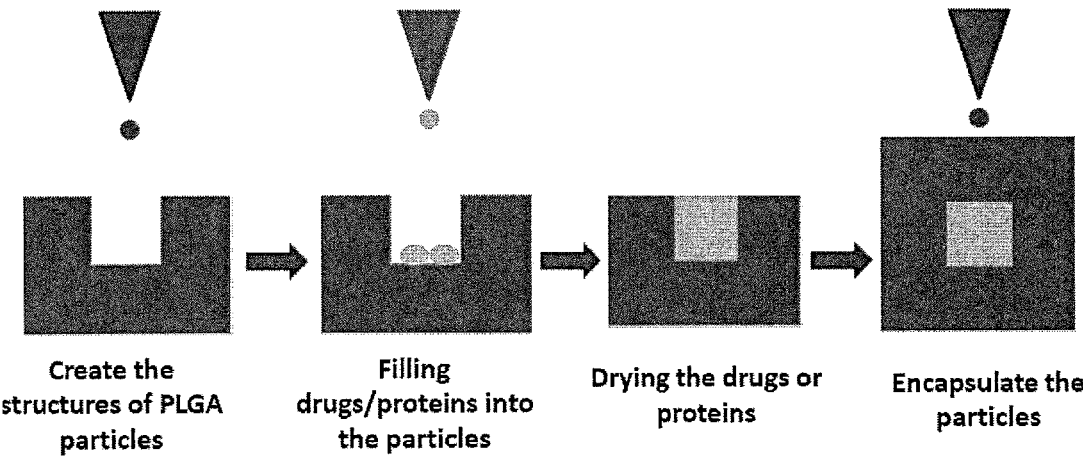
| Create the structures of PLGA particles | Filling drugs/proteins into the particles | Drying the drugs or proteins | Encapsulate the particles |
*First optimize printing in the x, y, and z directions by printing cube-shaped PLGA structures filled with vaccine.*
FIG. 12A          FIG. 12B          FIG. 12C          FIG. 12D week 1 serum data week 2 serum data

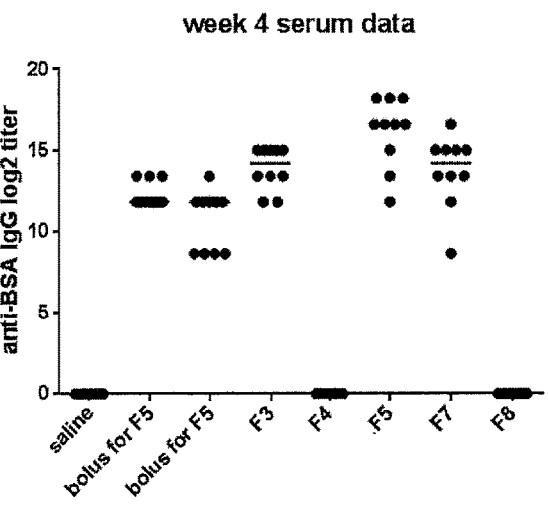
FIG. 19C
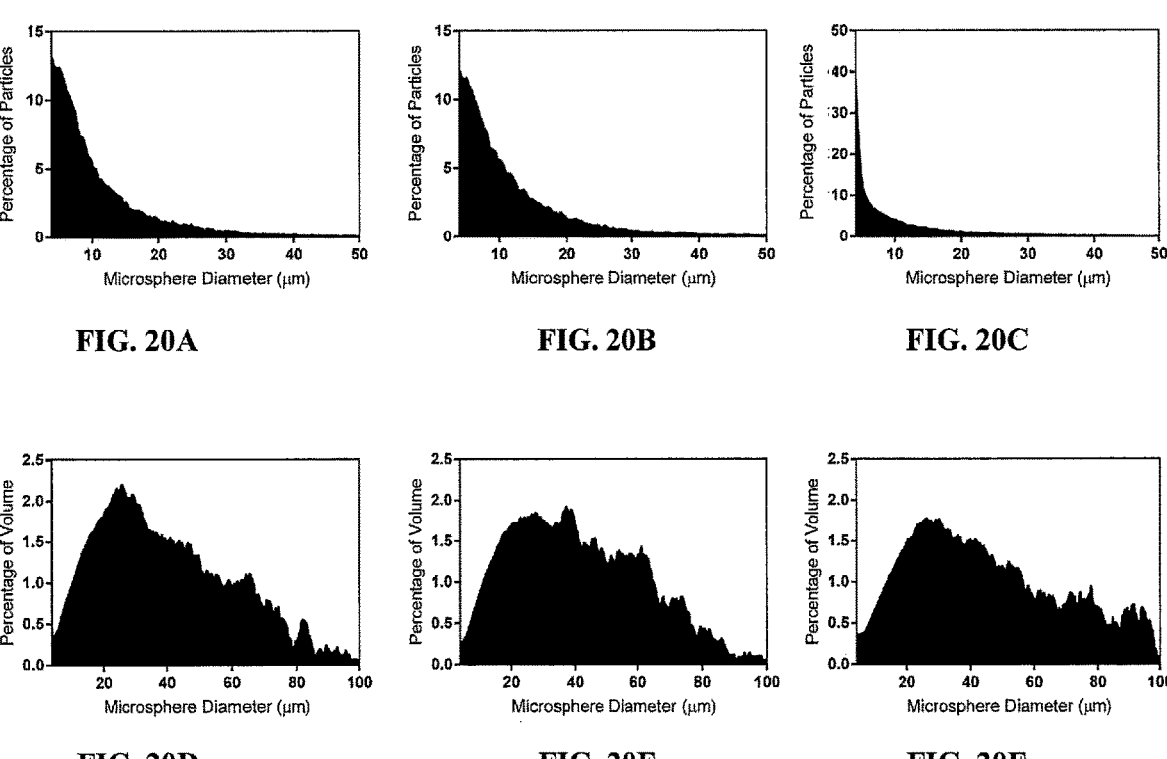
FIG. 20A       FIG. 20B       FIG. 20C
FIG. 20D       FIG. 20E       FIG. 20F

MICROMOLDED OR 3-D PRINTED PULSATILE RELEASE VACCINE FORMULATIONS

CROSS-REFERENCE TO RELATED APPLICATIONS

This application is a divisional of U.S. application Ser. No. 17/143,871, filed Jan. 7, 2021, which is a divisional of U.S. application Ser. No. 16/401,476, filed May 2, 2019, now U.S. Pat. No. 10,960,073, issued Mar. 30, 2021, which is a divisional of U.S. application Ser. No. 14/572,631, filed Dec. 16, 2014, now U.S. Pat. No. 10,300,136, issued May 28, 2019, which claims benefit of and priority to U.S. Provisional Application No. 61/916,555, filed Dec. 16, 2013, which are hereby incorporated herein by reference in their entirety.

FIELD OF THE INVENTION

This invention is generally in the field of injectable vaccine formulations providing multiple releases of vaccine.

BACKGROUND OF THE INVENTION

Vaccines typically involve an initial dose of antigen, followed by one or more booster doses at defined times after the initial administration, typically ten to 60 days later. The need for administration of a booster dose clearly limits the practicality of vaccines in much of the world, as well as increases costs and difficulties in agricultural applications.

Polymeric microspheres have the potential to be effective vaccine delivery vehicles. They have the ability to enhance targeting of antigen presenting cells (APCs) and have the potential for controlled, sustained release of antigen-thereby potentially eliminating the need for multiple vaccination doses. Further, the polymer matrix can act as a shield from a hostile external environment and has the potential to reduce adverse reactions and abrogate problems caused by the vaccine strain in immunocompromised individuals. PLGA microspheres have been developed for single immunization, with and without burst release. Given the biodegradable nature and sustained release properties that PLGA offers, microspheres formulated from PLGA could be useful for the delivery of vaccines. Summarized in Kirby et al., Chapter 13: Formation and Characterisiation of polylactide-co-galactide PLGA microspheres (2013). PLGA based microparticles are traditionally produced by double emulsion-solvent evaporation, nano-precipitation, cross-flow filtration, salting-out techniques, emulsion-diffusion methods, jet milling, and spray drying. Summarized in Kirby et al., Chapter 13: Formation and Characterisiation of polylactide-co-galactide PLGA microspheres (2013). PLGA microspheres can also be formulated to incorporate a range of moieties, including drugs and proteins, that can act as adjuvants. It has been contemplated that PGLA particles produced by these methods can be lyophilized and stored for later use and delivery.

Hanes et al., Adv. Drug. Del. Rev., 28:97-119 (1997), report on attempts to make polymeric microspheres to deliver subunit protein and peptide antigens in their native form in a continuous or pulsatile fashion for periods of weeks to months with reliable and reproducible kinetics, to obviate the need for booster immunizations. Microspheres have potential as carriers for oral vaccine delivery due to their protective effects on encapsulated antigens and their ability to be taken up by the Peyer's patches in the intestine.

The potency of these optimal depot formulations for antigen may be enhanced by the co-delivery of vaccine adjuvants, including cytokines, that are either entrapped in the polymer matrix or, alternatively, incorporated into the backbone of the polymer itself and released concomitantly with antigen as the polymer degrades.

As reported by Cleland et al., J. Controlled Rel. 47(2): 135-150 (1997), the administration of a subunit vaccine (e.g., gp120) for acquired immunodeficiency syndrome (AIDS) can be facilitated by a single shot vaccine that mimics repeated immunizations. Poly(lactic-co-glycolic acid) (PLGA) microspheres were made that provide a pulsatile release of gp120. Microspheres were made using a water-in-oil-in-water microencapsulation process with either methylene chloride or ethyl acetate as the polymer solvent. The protein was released under physiological conditions in two discrete phases: an initial burst released over the first day and after several weeks or months, a second burst of protein was released. The second burst of protein was dependent upon the PLGA inherent viscosity and lactide/glycolide ratio (bulk erosion).

These studies demonstrate that it is possible to achieve a vaccine response using injectable microparticles. However, no such product has ever been approved for human or animal use. It is difficult to achieve effective loading of antigen, uniformity of encapsulation and release, and extremely low levels of solvent not affecting antigenicity.

It is estimated that precluding the need for a "cold chain" for vaccine distribution through the development of thermostable formulations could save about $200 million annually. Trouble with implementing these strategies rests on the lack of appropriate cryprotectant methods. A Summarized in Kirby et al., Chapter 13: Formation and Characterisiation of polylactide-co-galactide PLGA microspheres (2013). Similar information and disclosure on nanovaccines can be found in Gregory et al., Frontiers in Cell and Infect. Microbio. 3:Article 13 (2013). Nandedkar, J. Biosci. 34:995-1003 (2009). Stabilization of proteins included in microspheres is problematic. A number of types of stabilizing excipients have been studied. Summarized in Kim and Pack, BioMEMS and Biomedical Nanotechnology. 1:19-50 (2006). Additionally, the type of polymer used for microsphere fabrication, its degradation rate, acidity of the degradation products, hydrophobicity, etc., can also impact the stability of incorporated proteins.

It is therefore an object of the present invention to provide injectable polymeric formulations providing release of encapsulated antigen at two or more times.

It is a further object of the present invention to provide injectable polymeric formulations which do not damage and which can stabilize encapsulated antigen.

It is a still further object of the present invention to provide methods and materials for micromolding and three-dimensional printing of injectable polymeric formulations providing release of encapsulated antigen at two or more times, and the resulting formulations.

SUMMARY OF THE INVENTION

Emulsion-based and Micromolded ("MM") or three dimensional printed ("3DP") polymeric formulations for single injection of antigen, preferably releasing at two or more time periods, have been developed. Formulations are preferably formed of biocompatible, biodegradable polymers. Discrete regions encapsulating antigen, alone or in combination with other antigens, adjuvants, stabilizers, and release modifiers, are present in the formulations. Antigen is preferably present in excipient at the time of administration, or on the surface of the formulation, for immediate release, and incorporated within the formulation for release at ten to 45 days after initial release of antigen, optionally at ten to 90 day intervals for release of antigen in one or more additional time periods. Antigen may be stabilized through the use of stabilizing agents such as trehalose glass. In a preferred embodiment for immunization against polio, antigen is released at the time of administration, and two, four and six months thereafter. In a preferred embodiment, leakage between bursts of release is minimal and release occurs over a narrow time frame.

Studies demonstrate the selection of polymer and solvent systems that provides for discrete release of antigen, without overlap, with minimal degradation or damage to the encapsulated antigen. Preferred solvents include methylene chloride and chloroform, and preferred polymers are polylactic acid ("PLA"), polyglycolic acid ("PGA"), and copolymers thereof ("PLGA").

Formulations are designed for subcutaneous or intramuscular injection via needle or cannula, for topical injection to a mucosal region such as intranasal, or by scarification to the epidermis. Preferred applications are for administration of antigen eliciting an effective immune response to infectious agents such as bacteria, virus, protozoan and parasitic organisms. However, formulations may also be used for administration of other therapeutic, prophylactic or diagnostic agents, alone or in combination with antigen.

BRIEF DESCRIPTION OF THE DRAWINGS

FIG. 3B, % BSA) over time (weeks) for 5% BSA and 0.5% BSA from PLLA, 50 kD.

FIG. 4B, % BSA) over time (weeks) for 5% BSA and 0.5% BSA from PLLA, 100 kD.

FIG. 5B, % BSA) over time (weeks) for 5% BSA and 0.5% BSA from PLLA, 300 kD.

FIG. 6B, % BSA) over time (weeks) for 5% BSA and 0.5% BSA from P(d,l)LA, 20 kD.

FIGS. 7A and 7B are graphs of protein release over time (weeks) for PLGA formulations (FIG. 7A) and bolus injections (FIG. 7B).

FIG. 8B, % BSA) over time (weeks) from PLGA (50:50), 20 kD, derivatized with a carboxylic group.

FIG. 9B, % BSA) over time (weeks) from PLGA (50:50), 31 kD, derivatized with a carboxylic group.

FIG. 10B, % BSA) over time (weeks) from PLGA (50:50), 31 kD, derivatized with a carboxylic group.

FIGS. 12A-12D are schematics of the 3D printing process: Creating the structure of PLGA particles (FIG. 12A), filling drugs or proteins into the particles (FIG. 12B), drying the drugs or proteins (FIG. 12C), and encapsulation of the particles (FIG. 12D).

(FIG. 15A) or 25° C. (FIG. 15B).

(FIG. 18A) or after lyophilization with 0.5 M trehalose-sucrose, pipetted, or 0.5 M trehalose-sucrose, jetted, then drying at 25° C., 10.7% RH (FIG. 18B).

FIGS. 19A-19C are graphs showing anti-BSA IgG (antibody) titers (in log 2 values) plotted for the groups presented in Table 3 at 1 week (FIG. 19A), 2 weeks (FIG. 19B), and 4 weeks (FIG. 19C) post-injection. The negative controls are all zero and the microsphere formulations are generating an equivalent or stronger response compared to the bolus control. (F4 and F8 are blank microspheres, no drug; see Table 4).

FIGS. 20A-20C are histograms showing size distribution of microspheres prepared with formulation C (FIG. 20A), formulation G (FIG. 20B), and formulation E (FIG. 20C).

FIGS. 20D-20F are histograms showing volume distribution of formulation C (FIG. 20D), formulation G (FIG. 20E), and formulation E (FIG. 20F).

FIG. 22A shows low-dose formulations C & G compared to a series of three dose-matched bolus BSA injections. FIG. 22B shows high-dose formulation E compared to its dose-matched bolus control. Bolus BSA was injected at 0, 4, and 8 weeks in the control groups. Filled symbols indicate significant differences between the group with unfilled symbols of the same shape and dose-matched control at that time point determined using ANOVA analysis for A (3 groups) and Student's t-test for B (2 groups). One, two, and three filled symbols indicate $p < 0.05$, $p < 0.01$, and $p < 0.001$ respectively and error bars represent standard deviation.

DETAILED DESCRIPTION OF THE INVENTION

I. Definitions

Figure 1:
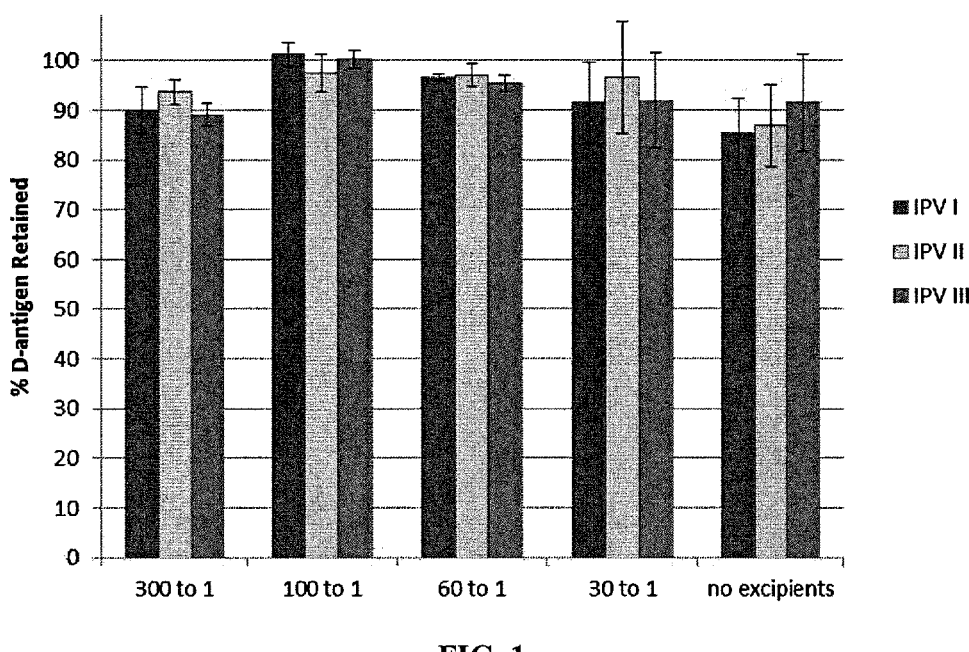
FIG. 1 is a bar graph showing the effect of lowering excipient:vaccine ratio on percentage of D-antigen retained after drying 26X Trivalent IPV on PLA for 16 hours at room temperature and humidity. Excipients: 10% sorbitol, 8.5% MSG, 8.5% MgCl$_2$.

"Additive manufacturing" or "3D printing" as used herein refers to a process of making a three-dimensional solid object of virtually any shape from a digital model. 3D printing is achieved using an additive process, where successive layers of material are laid down in different shapes or thicknesses. In some embodiments, "3D printing" involves an extruded or solvent based polymer-containing ink (e.g., PLGA, PLLA, etc.) that is jetted or extruded through a nozzle and solidified into a desired shape. The shape can be controlled in the x, y and z directions.

"Micromolding," as used herein, generally refers to processes suitable for manufacturing parts or devices on a microscale, or processes suitable for manufacturing parts or devices having features or tolerances on a microscale. Exemplary techniques include, but are not limited to, lithography.

"Microdevice," as used herein, refers to any object or device having microscale dimensions, such as 1 micron to 1000 microns, 1 micron to 500 microns, 1 micron to 250 microns, or 1 micron to 100 microns.

The term "diameter" is art-recognized and is used herein to refer to either of the physical diameter or the hydrodynamic diameter. The diameter of emulsion typically refers to the hydrodynamic diameter. The diameter of the capsules, both in spherical or non-spherical shape, may refer to the physical diameter in the hydrated state. The diameter of the particles, colloids and cells which are encapsulated inside the capsules refers to the physical diameter in the hydrated state. As used herein, the diameter of a non-spherical particle or a non-spherical capsule may refer to the largest linear distance between two points on the surface of the particle. When referring to multiple particles or capsules, the diameter of the particles or the capsules typically refers to the average diameter of the particles or the capsules. Diameter of particles or colloids can be measured using a variety of techniques, including but not limited to the optical or electron microscopy, as well as dynamic light scattering.

The term "biocompatible" as used herein refers to one or more materials that are neither themselves toxic to the host (e.g., an animal or human), nor degrade (if the material degrades) at a rate that produces monomeric or oligomeric subunits or other byproducts at toxic concentrations in the host.

The term "biodegradable" as used herein means that the materials degrades or breaks down into its component subunits, or digestion, e.g., by a biochemical process, of the material into smaller (e.g., non-polymeric) subunits.

The term "microspheres," "microparticles," or "microcapsules" is art-recognized, and includes substantially spherical solid or semi-solid structures, e.g., formed from biocompatible polymers such as subject compositions, having a size ranging from about one or greater up to about 1000 microns, such as 1 micron to 500 microns, 1 micron to 250 microns, or 1 micron to 100 microns. The term "microparticles" is also art-recognized, and includes microspheres and microcapsules, as well as structures that may not be readily placed into either of the above two categories, all with dimensions on average of less than about 1000 microns. A microparticle may be spherical or nonspherical and may have any regular or irregular shape. If the structures are less than about one micron in diameter, then the corresponding art-recognized terms "nanosphere," "nanocapsule," and "nanoparticle" may be utilized.

"Narrow range of release," as used herein, generally means that the agent is released over a specific period of time, such as an hour, hours, a day, a week, a month, etc.)

"Antigen" or "Vaccine," as used herein, refers to any molecule or entity that produces a specific immune response in a host organism, such as a mammal.

"Immune response," as used herein, refers to a specific response to an antigen or vaccine that produces immunity to any future exposure in a host, such as a mammal.

"Water soluble" generally refers to something that dissolves or comes apart in aqueous environment.

"Emulsion" as used herein refers to a liquid discrete phase homeogeneously dispersed in a liquid continuous phase.

"Hydrophilic," as used herein, refers to molecules which have a greater affinity for, and thus solubility in, water as compared to organic solvents. The hydrophilicity of a compound can be quantified by measuring its partition coefficient between water (or a buffered aqueous solution) and a water-immiscible organic solvent, such as octanol, ethyl acetate, methylene chloride, or methyl tert-butyl ether. If after equilibration a greater concentration of the compound is present in the water than in the organic solvent, then the compound is considered hydrophilic.

"Hydrophobic," as used herein, refers to molecules which have a greater affinity for, and thus solubility in, organic solvents as compared to water. The hydrophobicity of a compound can be quantified by measuring its partition coefficient between water (or a buffered aqueous solution) and a water-immiscible organic solvent, such as octanol, ethyl acetate, methylene chloride, or methyl tert-butyl ether. If after equilibration a greater concentration of the compound is present in the organic solvent than in the water, then the compound is considered hydrophobic.

II. Formulations

A. Polymers and Solvent Systems
Polymers

The formulations, which may be formed of microparticles, including microspheres or microcapsules and including those that are emulsion-based, or devices such as those prepared by micromolding, are formed of polymers. Antigen may be dispersed or encapsulated by the polymer. In one embodiment, the device contains a core that only contains one or more vaccines or antigen and stabilizers and the shell or particle wall only contains one or more biodegradable polymers with or without additives. Polymer without antigen may be used to seal or separate areas of the formulation from other areas, and release at different rates.

Polymers must be biocompatible and processible under conditions and using reagents that preserve the antigen. The formulation can be made with hydrophilic polymers, hydrophobic polymers, amphiphilic polymers, or mixtures thereof. The formulation can contain one or more hydrophilic polymers.

Hydrophilic polymers include cellulosic polymers such as starch and polysaccharides; hydrophilic polypeptides; poly (amino acids) such as poly-L-glutamic acid (PGS), gamma-polyglutamic acid, poly-L-aspartic acid, poly-L-serine, or poly-L-lysine; polyalkylene glycols and polyalkylene oxides such as polyethylene glycol (PEG), polypropylene glycol (PPG), and poly(ethylene oxide) (PEO); poly(oxyethylated polyol); poly(olefinic alcohol); polyvinylpyrrolidone); poly (hydroxyalkylmethacrylamide); poly(hydroxyalkylmethacrylate); poly(saccharides); poly(hydroxy acids); poly(vinyl alcohol), and copolymers thereof.

Examples of hydrophobic polymers include polyhydroxy-acids such as poly(lactic acid), poly(glycolic acid), and poly(lactic acid-co-glycolic acids); polyhydroxyalkanoates such as poly3-hydroxybutyrate or poly4-hydroxybutyrate; polycaprolactones; poly(orthoesters); polyanhydrides; poly (phosphazenes); poly(lactide-co-caprolactones); polycarbonates such as tyrosine polycarbonates; polyamides (including synthetic and natural polyamides), polypeptides, and poly(amino acids); polyesteramides; polyesters; poly (dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly (maleic acids), as well as copolymers thereof. In certain embodiments, the hydrophobic polymer is an aliphatic polyester. In preferred embodiments, the hydrophobic polymer is poly(lactic acid), poly(glycolic acid), or poly(lactic acid-co-glycolic acid).

The formulation can contain one or more biodegradable polymers. Biodegradable polymers can include polymers that are insoluble or sparingly soluble in water that are converted chemically or enzymatically in the body into water-soluble materials. Biodegradable polymers can include soluble polymers crosslinked by hydolyzable cross-linking groups to render the crosslinked polymer insoluble or sparingly soluble in water.

Biodegradable polymers include polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly (methyl methacrylate), poly(ethylmethacrylate), poly (butylmethacrylate), poly(isobutylmethacrylate), poly(hexlmethacrylate), poly(isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene poly (ethylene glycol), poly(ethylene oxide), poly(ethylene terephthalate), poly(vinyl alcohols), poly(vinyl acetate, poly vinyl chloride polystyrene and polyvinylpyrrolidone, derivatives thereof, linear and branched copolymers and block copolymers thereof, and blends thereof. Exemplary biodegradable polymers include polyesters, poly(ortho esters), poly(ethylene imines), poly(caprolactones), poly (hydroxybutyrates), poly(hydroxyvalerates), polyanhydrides, poly(acrylic acids), polyglycolides, poly(urethanes), polycarbonates, polyphosphate esters, polyphosphazenes, derivatives thereof, linear and branched copolymers and block copolymers thereof, and blends thereof.

Amphiphilic polymers can be polymers containing a hydrophobic polymer block and a hydrophilic polymer block. The hydrophobic polymer block can contain one or more of the hydrophobic polymers above or a derivative or copolymer thereof. The hydrophilic polymer block can contain one or more of the hydrophilic polymers above or a derivative or copolymer thereof.

In particularly preferred embodiments the microparticle contains biodegradable polyesters or polyanhydrides such as poly(lactic acid), poly(glycolic acid), and poly(lactic-co-glycolic acid). The microparticles can contain one more of the following polyesters: homopolymers including glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA," and caprolactone units, such as poly(ε-caprolactone), collectively referred to herein as "PCL;" and copolymers including lactic acid and glycolic acid units, such as various forms of poly(lactic acid-co-glycolic acid) and poly(lactide-co-glycolide) characterized by the ratio of lactic acid:glycolic acid, collectively referred to herein as "PLGA;" and polyacrylates, and derivatives thereof. Exemplary polymers also include copolymers of polyethylene glycol (PEG) and the aforementioned polyesters, such as various forms of PLGA-PEG or PLA-PEG copolymers, collectively referred to herein as "PEGylated polymers." In certain embodiments, the PEG region can be covalently associated with polymer to yield "PEGylated polymers" by a cleavable linker.

The formulation can contain one or a mixture of two or more polymers. The microparticles may contain other entities such as stabilizers, surfactants, or lipids.

Solvents

Solvents must be biocompatible, since some residue will always be present in the polymeric formulations. Representative polymer solvents include organic solvents such as chloroform, dichloromethane, tetrafluoroethylene, and acyl acetate. The antigen can be dissolved in aqueous or aqueous miscible solvents such as acetone, ethanol, methanol, isopropyl alcohol, and mixtures thereof.

B. Therapeutic, Prophylactic, Nutriceuticals, and Diagnostic Agents

Although described with reference to delivery of vaccines, it will be understood that the formulations may be used to provide release of a variety of therapeutic, prophylactic, nutriceutical, and/or diagnostic agents. These agents may be low molecular weight drugs, proteins such as hormones or growth factors, immunomodifiers, antibodies, nucleic acid molecules (DNA, RNA, microRNA, siRNA).

Antigen

Infectious Agents

Antigens for delivery are killed or attenuated infectious agents such as bacteria such as Clostridia tetani, viruses such as hepatitis, influenza, and polio, and protozoans such as Plasmodium (malaria) and Leishmania. Table 2 lists some vaccines the antigens of which can be used in the disclosed formulations. Other antigens are antigenic proteins or haptens such as carbohydrate or sugar antigens effective as antigens for these infectious agents, as cancer antigens, or as immunostimulants.

Poliomyelitis (Polio) is a highly contagious viral disease that invades the nervous system and can cause total paralysis in a matter of hours. One in 200 infections leads to irreversible paralysis, which is usually confined to the legs. Among those paralyzed, 5% to 10% die due to paralysis of the diaphragm. There is no cure for polio. However, it can be prevented by vaccination.

Polio cases have decreased by over 99% since 1988, from an estimated 350,000 cases in more than 125 endemic countries to only 223 reported cases in 2012. As of early 2013, only three countries (Afghanistan, Nigeria, and Pakistan) in the world were endemic for the disease. Despite aggressive vaccination efforts, polio has not been completely eradicated and outbreaks still occur, particularly in developing countries.

There are two types of vaccine that protect against polio: Inactivated Polio Vaccine (IPV) and Oral Polio Vaccine (OPV). To be effective, the IPV needs to be administered to the blood stream. In contrast, the OPV is effective by crossing intestinal epithelium. While the OPV confers superior intestinal immunity, is easy to administer, and is low in cost, live poliovirus is shed by the vaccinated. This is a concern where the entire population is not vaccinated.

As such, use of an IPV is preferable.

Cancer Antigens

Any protein produced in a tumor cell that has an abnormal structure due to mutation can act as a tumor antigen. Such abnormal proteins are produced due to mutation of the concerned gene. Mutation of protooncogenes and tumor suppressors which lead to abnormal protein production are the cause of the tumor and thus such abnormal proteins are called tumor-specific antigens. Examples of tumor-specific antigens include the abnormal products of ras and p53 genes. In contrast, mutation of other genes unrelated to the tumor formation may lead to synthesis of abnormal proteins which are called tumor-associated antigens.

Proteins that are normally produced in very low quantities but whose production is dramatically increased in tumor cells, trigger an immune response. An example of such a protein is the enzyme tyrosinase, which is required for melanin production. Normally tyrosinase is produced in minute quantities but its levels are very much elevated in melanoma cells.

Oncofetal antigens are another important class of tumor antigens. Examples are alphafetoproteins (AFP) and carcinoembryonic antigen (CEA). These proteins are normally produced in the early stages of embryonic development and disappear by the time the immune system is fully developed. Thus self-tolerance does not develop against these antigens.

Abnormal proteins are also produced by cells infected with oncoviruses, e.g., Epstein Barr Virus ("EBV") and Human Papillomavirus ("HPV"). Cells infected by these viruses contain latent viral DNA which is transcribed and the resulting protein produces an immune response. In addition to proteins, other substances like cell surface glycolipids and glycoproteins may also have an abnormal structure in tumor cells and could thus be targets of the immune system.

Many tumor antigens have the potential to be effective as tumor vaccines. In addition to alpha fetoprotein (germ cell tumors, hepatocellular carcinoma) and carcinoembryonic antigen (bowel, lung, breast cancers), examples of tumor antigens include CA-125 (ovarian cancer), MUC-1 (breast cancer, epithelial tumor antigen (breast cancer), and melanoma-associated antigen (malignant melanoma).

C. Stabilizing Agents

Antigen stability is defined as the maintenance of antigen structure during formation of the vaccine formulation and at body temperature. As discussed below, the polymer composition, selection of solvent, and processing conditions are critical to maintain antigen stability.

Stabilizing agents may also be added. Sugars are a typical group of stabilizing agents for proteins. Examples include simple sugars such as sucrose, fructose, mannitol, glucose, and trehalose as well as more complex sugars. See Alcock et al., Long-term thermostabilization of live poxviral and adenoviral vaccine vectors at supraphysiological temperatures in carbohydrate glass. Science Translational Medicine, 2(19):19-19ra12 (2010).

Stabilization of the antigen can be determined by antigen specific ELISA in vitro and by measuring the immune response (e.g., IgGs) in animals in vivo. Stability is evaluated during each step of the encapsulation and/or manufacturing process, during storage (at 25° C., room temp, high humidity/high temp conditions, under physiological conditions (pH 7.2, 37° C.) and in vivo (animal models).

D. Agents Increasing Rate or Completeness of Release

Gas-generated burst-release systems may allow for instantaneous release of encapsulated antigen. Pore forming agents which are removed by leaching or lyophilization may also be utilized.

III. Methods of Manufacture

It is essential that the methods used to manufacture the device maintain antigen stability, both during processing and at body temperature, and that leakage following formation and administration are minimized. Post-formulation sterilization can typically be accomplished through a combination of sterile manufacturing conditions in combination with methods such as gamma irradiation.

A. Emulsion

Microparticles can be made using standard techniques. A preferred technique is emulsification of a polymer solution in an organic solvent with an aqueous solution. Addition of organic phase to a large volume of non-solvent phase forms a spontaneous single emulsion and the resulting solution is stirred continuously for solvent evaporation. Immediate formation of microspheres occurs. After stirring, microspheres are washed and then dried.

The examples demonstrate formation of microparticles using emulsification of polymer and antigen, alone or in combination with stabilizers such as trehalose and sucrose.

B. Three Dimensional Printing 3D printing could increase consistency of microspheres, allowing for more uniform release, as well as provide a means for making more complex devices such as 'Micro-rods', having increased carrying capacity, that could eliminate the need for simultaneous release from multiple microspheres, as well as facilitate scale up.

Three-dimensional (3D) printing is a process of making 3D objects from a digital model. 3D printing is an additive process, where successive layers of material are laid down in different shapes. After each layer is added the "ink" is polymerized, typically by photopolymerization, and the process repeated until a 3D object is created. The recent commercial availability and reduced cost makes 3D printing of biomolecules, including vaccines and pharmaceuticals, attractive for distribution of these compounds to developing countries. This would negate the need to ship a finished product into the country. Instead, a 3D printer at the point of care can print out the required biomolecule from a simple computer program, which can come from anywhere in the world.

The 3D printing workflow can be described in 3 sequential steps: 1) the powder supply system platform is lifted and the fabrication platform is lowered one layer; 2) a roller spreads the polymer powder into a thin layer; 3) a print-head prints a liquid binder that bonds the adjacent powder particles together. Billiet et al., *Biomaterials,* 33:6020-6041 (2012). Two kinds of 3D printing techniques are mostly adopted for nanobiomaterial fabrication. One is inkjet printing with the typical printers. Marizza et al., *Microelectrionic Engin.* 111:391-395 (2013). The other is nanoimprint lithography.

Nanoimprint lithography (NIL) is a fast and cost-efficient technique for fabricating nanostructures. The procedure of NIL is to stack multiple layers of such structures on top of each other; that is, a finished double-layer of structures is covered with a spacer-layer which is planarized using the chemical-mechanical polishing so that a second layer can be processed on top. Liu et al., *J. Nanomat.* August (2013).

Ink-Jet printing has been used to produce monodisperse PLGA particles. Bohmer et al., *Colloids and Surfaces A: Physiochem. Eng. Aspects,* 289:96-104 (2006). Briefly, droplets of a PLGA solution are printed with the ink-jet nozzle submerged into an aqueous phase. This method produces microspheres at predictable and controllable sizes. This technique has been used to created Paclitaxel-loaded monodisperse microspheres. Radulecu et al., *Digital Fabrication* September:18-21. (2005). Variation of this technology has been used to create multilayer monodisperse microspheres. See Kim and Pack, *BioMEMS and Biomedical Nanotechnology,* 1:19-50 (2006). Utilizing this technology, microcapsule shell thickness can be varied from less than 2 microns to tens of microns while maintaining complete and well-centered core encapsulation for microcapsules near 50 microns in overall diameter.

Drug delivery rates from microspheres have been varied by providing uniform monodisperse microparticles, mixtures of microparticles of varying sizes, and microparticles having different degradable layers. See Kim and Pack, *BioMEMS and Biomedical Nanotechnology,* 1:19-50 (2006).

Additional information can be found at internet site store.makerbot.com/replicator2 (2013); Tekin et al., Inkjet printing as a deposition and patterning tool for polymers and inorganic particles. *Soft Matter,* 4:703-713 (2008); Jang et al., Influence of fluid physical properties on ink-jet printability. *Langmuir,* 25:2629-2635 (2009); Lan, Design and Fabrication of a Modular Multi-Material 3D Printer., M.Sc. Thesis: Massachusetts Institute of Technology, 2013; and at web site imagexpert.com/site-new/pdf/IXjetXpert.pdf. (2013).

The examples demonstrate preparation of microparticles using 3DP. Waveform was optimized for jetting monodisperse ink droplets consistently. The applied voltage, the duration of the applied voltage, and the change in voltage over time (slope) are all parameters that must be optimized to jet high quality ink drops. For example, the waveform was optimized for a solution of 5% w/v 31k (average molecular weight) PLGA in 1,4-dioxane. Waveforms were optimized with the JetXpert imaging system, and the ink and waveform and then transferred to the multi-material inkjet 3D-printer. JetXpert imaging was done with a constant pressure waveform. In one embodiment, 5% w/v 31k PLGA/1,4-dioxane (Z=5.3, η=6.08 mPa-s) was used. The waveform was optimized for this specific solution. In another embodiment, 15% w/v 12k PLGA/1,2-dichloroethane (Z=5.8, η=6.24 mPa-s) was used. Most nozzles showed optimal jetting as in the first embodiment, with very few nozzles giving sequences containing satellite drops. In a third embodiment, 15% w/v 12K PLGA/chloroform (Z=5.8, η=5.99 mPa-s) was used (Table 1). When using more volatile solvents (chloroform or acetone), most nozzles fired more than one drop continuously. In general, for a constant optimized waveform and similar fluid properties, inks made with more volatile solvents led to inconsistent jetting, and print head nozzles would clog during printing (observed when using 1,2-dichloroethane or chloroform). Inks can be made with 1,4-dioxane and DMF, to prevent nozzles from clogging. Printing with these solvents requires longer drying time between layers, to prevent structures from morphing. As determined by GPC, for a given polymer, increasing the polymer concentration in the ink increased the ink viscosity. For a given polymer concentration, increasing the molecular weight range of the polymers increased the ink viscosity. After polymer addition, changes observed in ink densities and surface tensions were negligible relative to viscosity changes.

TABLE 1

Solvents for 3DP.

| Mw Range/ Solvent | % w/v | Density (g/ml) | Surface Tension (mN/m) | Viscosity (mPa-s) | Z number (dimension- less) |
|---|---|---|---|---|---|
| 4 k-15 k/ | 5% | 1.45 | 28.07 | 1.42 | 24.6 |
| Chloroform | 10% | 1.43 | 27.93 | 3.17 | 10.9 |
|  | 15% | 1.44 | 27.67 | 5.03 | 6.9 |
| 7 k-17 k/ | 5% | 1.45 | 27.99 | 2.26 | 15.4 |
| Chloroform | 10% | 1.41 | 27.74 | 3.64 | 9.4 |
|  | 15% | 1.43 | 28.26 | 5.99 | 5.8 |
| 24 k-38 k/ | 5% | 1.45 | 28.12 | 3.60 | 9.7 |
| Chloroform | 10% | 1.40 | 27.77 | 9.32 | 3.7 |
|  | 15% | 1.44 | 28.70 | 26.3 | 1.3 |
| 4 k-15 k/ | 5% | 1.28 | 33.31 | 2.26 | 15.8 |
| 1,2-dichloroethane | 10% | 1.28 | 32.92 | 3.65 | 9.7 |
|  | 15% | 1.27 | 33.68 | 5.58 | 6.4 |
| 7 k-17 k/ | 5% | 1.28 | 33.69 | 2.35 | 15.3 |
| 1,2-dichloroethane | 10% | 1.25 | 32.17 | 3.88 | 9.0 |
|  | 15% | 1.29 | 33.95 | 6.24 | 5.8 |
| 24 k-38 k/ | 5% | 1.26 | 32.36 | 3.94 | 8.9 |
| 1,2-dichloroethane | 10% | 1.30 | 33.90 | 13.8 | 2.6 |
|  | 15% | 1.27 | 33.68 | 49.1 | 0.7 |
| 24 k-38 k/ 1,4-dioxane | 5% | 1.09 | 31.52 | 6.08 | 5.3 |
| 24 k-38 k/ dimethylformamide | 5% | 0.97 | 36.60 | 5.50 | 5.9 |

Figures 11A, 11B, 11C, 11D, 11E:
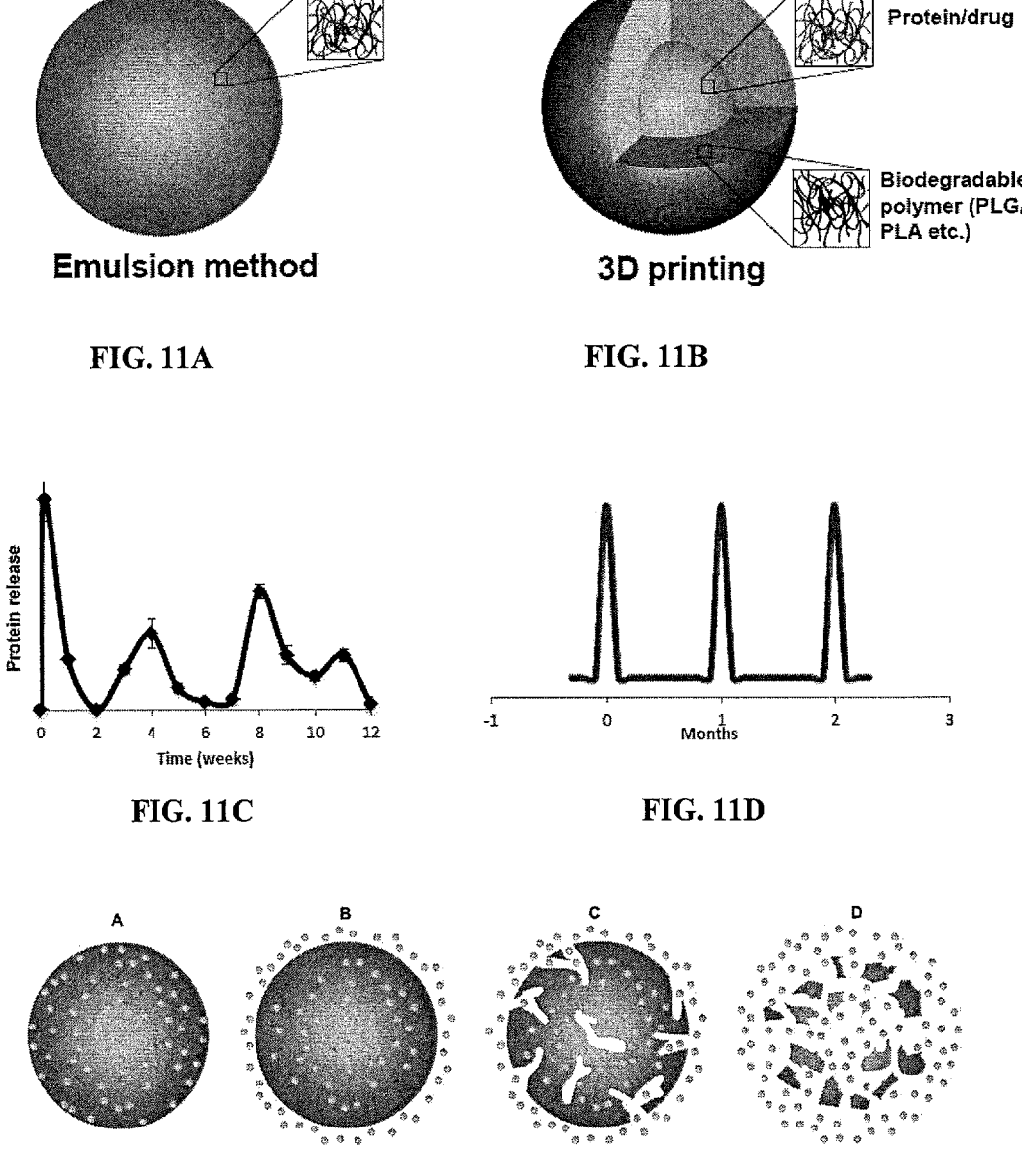
FIGS. 11A and 11B are schematics of particles made by emulsion (FIG. 11A) and by 3D printing or micromolding (FIG. 11B), and the release of protein from the emulsion particle (FIG. 11C) and the 3DP particle (FIG. 11D), which models the release of protein from bolus injections.
FIG. 11E is a schematic of polymer degradation-based bursts with one month lag to simulate bolus injections.

FIGS. 11A and 11B are schematics of particles made by emulsion (FIG. 11A) and by 3D printing (FIG. 11B), and the release of protein from the emulsion particle (FIG. 11C) and in an ideal case the 3DP particle (FIG. 11D). These show the differences in the resulting structure, which also changes the release kinetics.

Figures 22A, 22B, 23A, 23B, 24A, 24B, 24C:
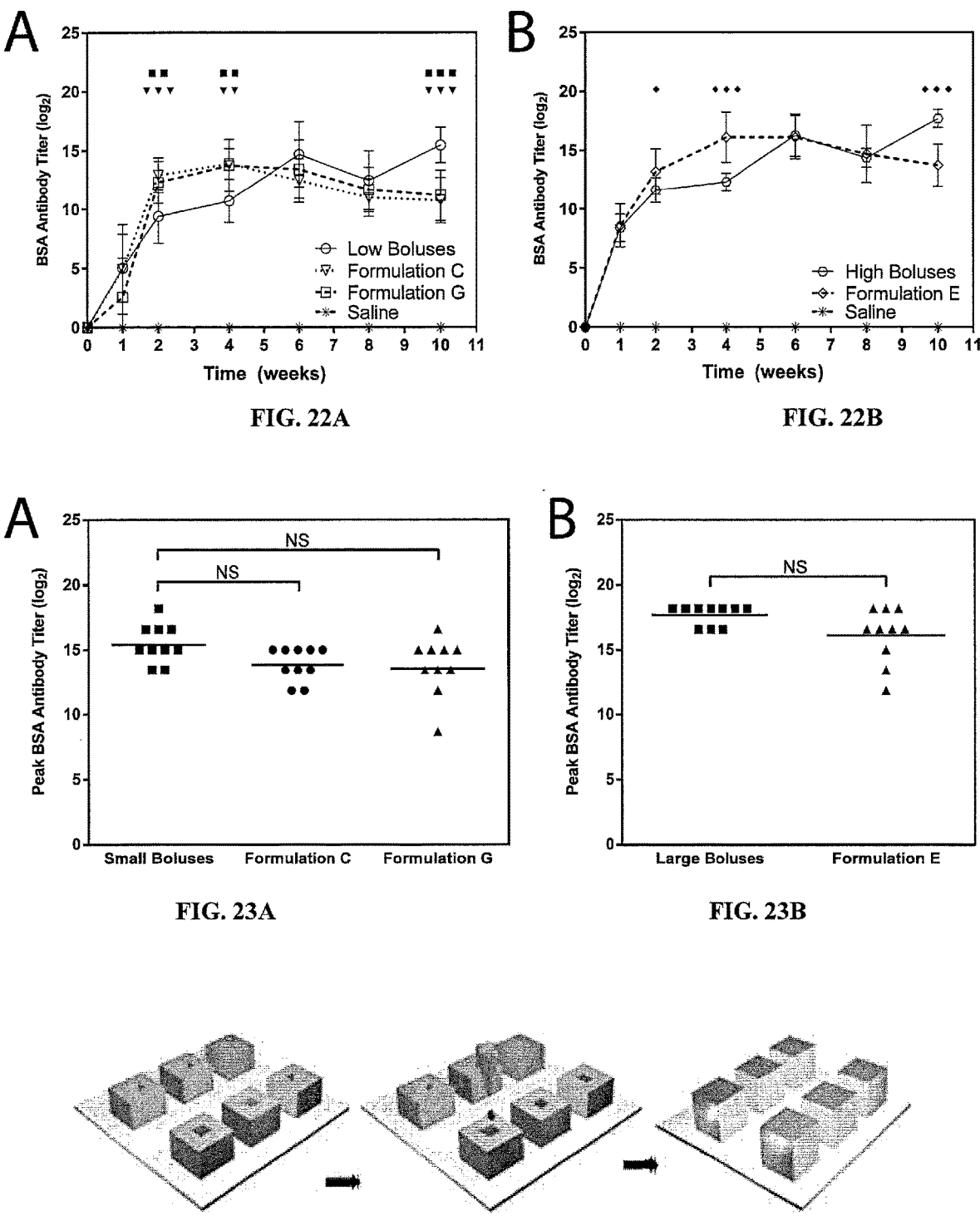
FIGS. 22A and 22B are line graphs showing IgG antibody titers in mouse sera against BSA released from microparticles and plotted as geometric mean over time on a log 2 scale.
FIGS. 23A and 23B are dot plots showing peak titers induced by immunization at low (FIG. 23A), and high (FIG. 23B) BSA dosing. Peak titers for all microparticle formulations occurred at week 4 while both bolus injection groups peaked at week 10. NS represents not significant when using a Student's t-test with Holm-Bonferroni correction for multiple comparisons at a significance level of 0.05. Adjusted p values for formulations C, G, and E are 0.0645, 0.0543, and 0.0784 respectively.
FIGS. 24A-24C are schematics of the micromolding process showing the steps of shell microfabrication (FIG. 24A), the filling of shells with drug (FIG. 24B), and sealing the shell with a cap (FIG. 24C).

FIGS. 12A-12D are schematics of the 3D printing process: Creating the structure of PLGA particles (FIGS. 12A and 24A), filling drugs or proteins into the particles (FIGS. 12B and 24B), drying the drugs or proteins (FIG. 12C), and encapsulation of the particles (FIGS. 12D and 24C). The schematic shows a cube shaped structure filled with vaccine, but it is understood that a mold may be utilized to provide any shaped, and that the mold may be filled in layers or more complex patterns.

Figure 13:
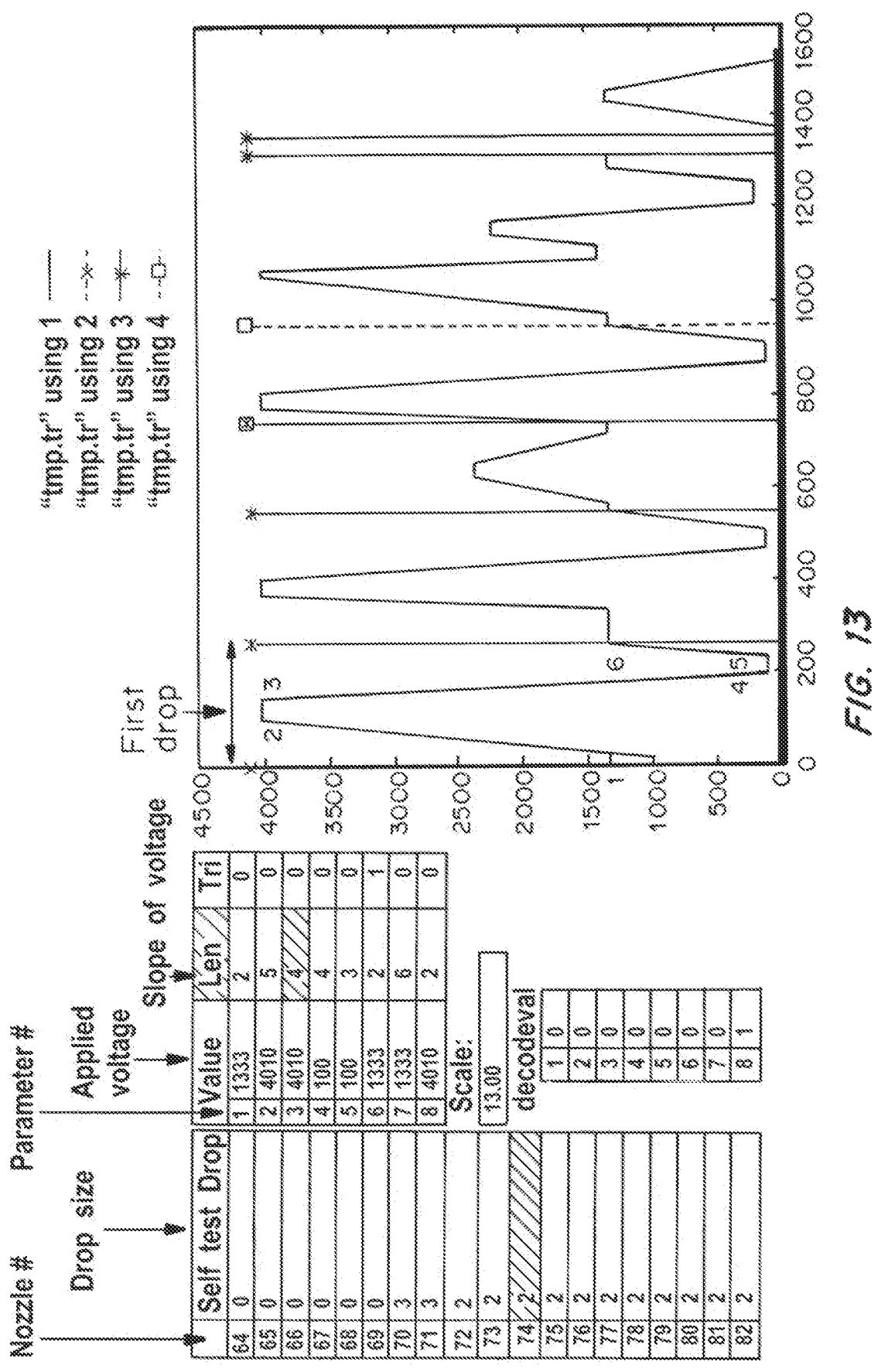
FIG. 13 is a schematic of the waveform parameters to be optimized to produce uniform single droplets of "ink" (polymer solution) during printing from a piezoelectric nozzle jet.

Waveform parameters can be optimized to produce uniform single droplets of "ink" (polymer solution) during printing from a piezoelectric nozzle jet (FIG. 13). Drop size is a function of various parameters which are optimized, including applied voltage, slope of voltage, polymer and solvent selection and concentration.

C. Micromolding

Park et al., *Biomed. Microdevices*, 9:223-234 (2007), describes using micromolding to fabricate polymer microstructures having sophisticated designs. Micromolds were filled with polymer microparticles, to produce microstructures composed of multiple materials, having complex geometries, and made using mild processing conditions. These microparticles are typically prepared using an oil-water, double-emulsion system; spray drying methods; supercritical conditioning methods; and milling methods. In a preferred embodiment, micromolds can be prepared by photolithographically creating a female master mold made of photoresist, molding a male master structure out of polydimethylsiloxane (PDMS) from the female master mold and) molding a female replicate mold out of PDMS from the male master structure. Polymer microparticles can be micromolded using temperature/press methods and/or from solvent.

Polymeric microparticles of 1 to 30 μm in size were made from PLA, PGA and PLGA using spray drying and emulsion techniques. These polymer microparticles were filled into PDMS micromolds at room temperature and melted or bonded together, for example, by ultrasonically welding microparticles together in the mold while maintaining the voids inherent in their packing structure. Multi-layered microstructures were fabricated to have different compositions of polymers and encapsulated compounds located in different regions of the microstructures. Molds were filled with solid polymer microparticles instead of a polymer melt to copy microstructures with complex geometries and composed of multiple materials using mild processing conditions. Microparticles can flow easily into the cavities of micromolds at room temperature and low pressure, which facilitates making microstructures with high aspect ratios. Moreover, polymer microparticles can encapsulate chemical compounds, such as drugs, and can be filled into molds in sequential layers to accommodate multiple material compositions. After filling the mold, the final microstructures can be created by welding the microparticles within the mold by plastic welding methods, including thermal and ultrasonic welding as well as solvent and gas based welding.

These same techniques can be used to formulate vaccine formulations, once has identified the polymeric materials and conditions required to obtain a narrow time of release at specific time points following administration.

IV. Methods of Administration

The vaccine formulations are administered to an individual in need of vaccination. These are administered as a dosage formulation including an effective amount of one or more antigens released in a schedule that elicits a protective effect against the source of the antigen.

Microparticles or microcapsules can be administered by injection, preferably subcutaneously or intramuscularly, for example, under the skin of the back of the upper arm, or to a mucosal surface (orally, intranasally, via the pulmonary route, or other orifice), although injection is preferred if release is to occur over a prolonged period of time of more than a few days.

The dosage form is designed to release a bolus of antigen at the time of administration. This may be achieved by administering a solution or dispersion of antigen in combination with the vaccine formulation providing multiple releases at subsequent times, or the device may be formulated to provide an initial bolus as well as subsequent release(s).

Representative vaccines are shown in Table 2:

| Age ► Vaccine ▼ | Birth | 1 month | 2 months | 4 months | 6 months | 12 months | 15 months | 18 months | 19-23 months |
|---|---|---|---|---|---|---|---|---|---|
| Hepatitis B[1] | HepB | HepB | | | | | HepB | | |
| Rotavirus [2] | | | RV | RV | RV[2] | | | | |
| Diphtheria, Tetanus, Pertussis[3] | | | DTaP | DTaP | DTaP | See footnote[3] | DTaP | | |
| Heamophilius influenza type b[4] | | | Hib | Hib | Hib[4] | Hib | | | |
| Pneumococcal[5] | | | PCV | PCV | PCV | PCV | | | |
| Inactivated Poliovirus[6] | | | IPV | IPV | | IPV | | | |
| Influenza[7] | | | | | | Influenza (Yearly) | | | |
| Measles, Mumps, Rubella[8] | | | | | | MMR | See footnote[8] | | |
| Varicella[9] | | | | | | Varicella | See footnote[9] | | |
| Hepatitis A[10] Meningococcal[10] | | | | | | HepA (2 doses) | | | |

Additional vaccines of great interest in third world countries include polio and smallpox. The following uses polio vaccine as an exemplary vaccine for this application.

IPV Vaccine SSI is an inactivated vaccine used for prophylactic vaccination against paralytic poliomyelitis. IPV Vaccine SSI contains inactivated poliovirus type 1, 2 and 3, propagated in Vero cells.

Contents per dose (0.5 ml):

Inactivated poliovirus type 1 (Brünhilde) 40 D-antigen units;

Inactivated poliovirus type 2 (MEF-1) 8 D-antigen units;

Inactivated poliovirus type 3 (Saukett) 32 D-antigen units;

Medium 199 to 0.5 ml.

The vaccine is manufactured without use of serum and trypsin and does not contain preservatives or adjuvants. Antibiotics are not used in the manufacture. IPV Vaccine SSI contains trace amounts of residual formaldehyde. It is manufactured in Denmark by Statens Serum Institut.

IPV Vaccine SSI is a solution for injection distributed in single-dose vials. For primary vaccination a series of three doses of 0.5 ml is administered.

For booster vaccination of previously primary vaccinated persons one dose of 0.5 ml is administered, at the earliest 6 months after the primary vaccination series. Administration of additional booster doses should take place in accordance with national recommendations for polio immunization. The vaccine should be administered intramuscularly or subcutaneously. The vaccine must not be administered intravascular. The age at the first dose should be at least 6 weeks, and the primary vaccination series should include at least three immunizations, with an interval of at least four weeks. Most countries give IPV using the same schedule as DPT vaccine (typically 2 months, 4 months, and 6 months of age).

The immunogenicity and safety of IPV Vaccine SSI has been investigated in several clinical trials, including clinical trials with combined vaccines for pediatric use. Apart from IPV these trials included vaccine antigens against tetanus, diphtheria, pertussis and Haemophilus influenzae type b.

When initiating immunizations at two months of age, completion of a primary vaccination series of three immunizations with at least 1 month interval can be expected to result in seroconversion to all three types of poliovirus one month after the second immunization. When initiating immunizations before two months of age, and at the earliest at 6 weeks of age, seroconversion rates between 89% and 99% have been demonstrated. Therefore, in such a schedule, a booster dose at 9 months of age or in the second year of life should be considered.

IPV Vaccine SSI can be used for revaccination in infants, pre-school aged children and adults primary immunized with IPV or OPV. IPV Vaccine SSI can be used in mixed IPV/OPV schedules, using one to three doses of IPV followed by one to three doses of OPV. It is recommended to administer IPV before the first dose of OPV. In a mixed IPV/OPV schedule, persistence of protective antibodies after primary vaccination has been shown to last at least 20 years. In an IPV only schedule the persistence of protective SSI recommended dose:

D-antigen type 1—40 DU/ml

D-antigen type 2—8 DU/ml

D-antigen type 3—32 DU/ml

10× Trivalent IPV:

D-antigen type 1—327 DU/ml

D-antigen type 2—70 DU/ml

D-antigen type 3—279 DU/ml

The present invention will be further understood by the following non-limiting examples.

EXAMPLES

The examples below describe different polymer-drug or polymer-antigen formulations for controlled release of the drug/antigen. The controlled release relies on polymer degradation to achieve multiple bursts of drug/antigen release over time following single injection. Immunogenicity of the formulations following polymer degradation-based bursts of drug/antigen release and sustained increase in anti-antigen antibody titer are also presented. Methods of making the formulations, which include incorporation of the antigen into the polymer matrix via spontaneous emulsion, or encapsulation of the antigen within a polymer shell via 3D printing or micromolding, are also described. Studies on improving the stability of the antigen, the stability of the polymer matrix, and the stability of the formulations, so that formulations with desired release characteristics and immunogenicity can be obtained, are also presented.

Example 1: Selection of Polymers and Solvents for Discrete Release of Vaccine

Materials and Methods

Polymer type—PLGA, PLLA; polymer $M_w$—9.5k, 20k, 31k, 46k

Drug loading—0.5, 3, 5%; excipients—trehalose, sucrose
Encapsulation—Spontaneous Emulsion The process used $CH_2Cl_2$:TFE::4:1.($CH_2Cl_2$—dichlo-romethane TFE—trifluoroethanol) as the organic phase, with poly(vinyl alcohol) ("PVA") to encapsulate 5%, 3% or 0.5% bovine serum albumin ("BSA") or inactivated polio virus ("IPV") into the polymer. The addition of the organic phase to a large volume of a non-solvent phase forms a spontaneous single emulsion and the resulting solution is stirred continuously to evaporate the solvent. Immediate formation of microspheres occurs. After stirring, the microspheres are washed and then dried. See Jaklenec et al., Sequential release of bioactive IGF-I and TGF-β1 from PLGA microsphere-based scaffolds. *Biomaterials*, 29(10): 1518-1525 (April 2008).

Release studies were done in vitro with 10 mg of microspheres suspended in 1 ml of PBS buffer (pH 7.2) at 37° C. Time points where taken at day 1, 4, 7 and every week thereafter. At each time point, the vials were centrifuged, the supernatant was removed to be assayed, a fresh 1 ml of PBS was added and the pelleted microspheres were resuspended.

Results

Figure 21A:
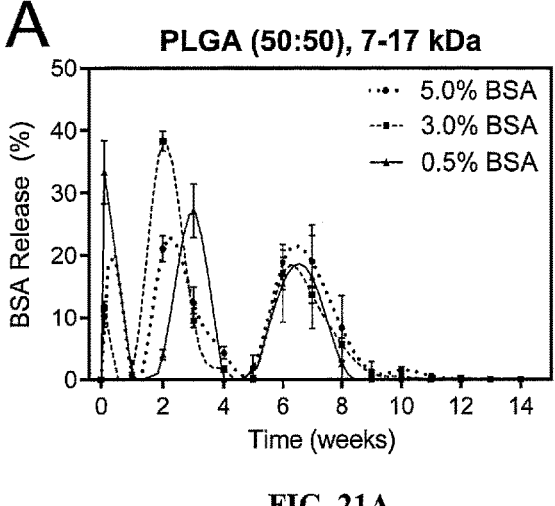
FIGS. 21A-21D are line graphs showing weekly BSA release (in percentages (%)) from microspheres formulated with 7-17 kDa, 50:50 PLGA (FIG. 21A), 24-38 kDa, 50:50 PLGA (FIG. 21B), 38-54 kDa, 50:50 PLGA (FIG. 21C), and 4-15 kDa, 75:25 PLGA (FIG. 21D) containing 0.5, 3, or 5% BSA by weight. Error bars represent standard deviation.

FIG. 21A is a graph of the release of a model protein, bovine serum albumin ("BSA") over time (weeks) for 5% BSA, 3% BSA, and 0.5% BSA from PLGA (50:50), 20 kD, derivatized with a carboxylic group.

Figure 21B:
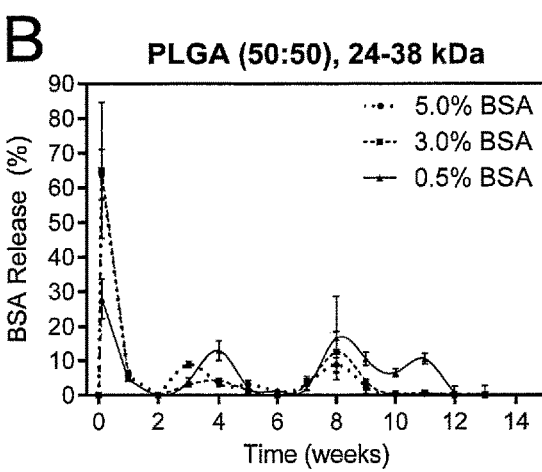
Figure 21C:
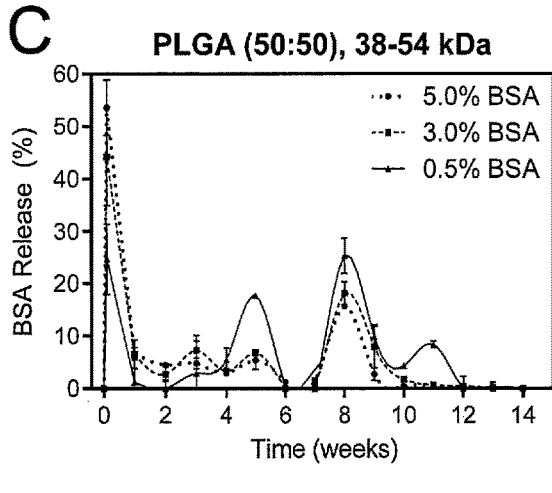
Figure 21D:
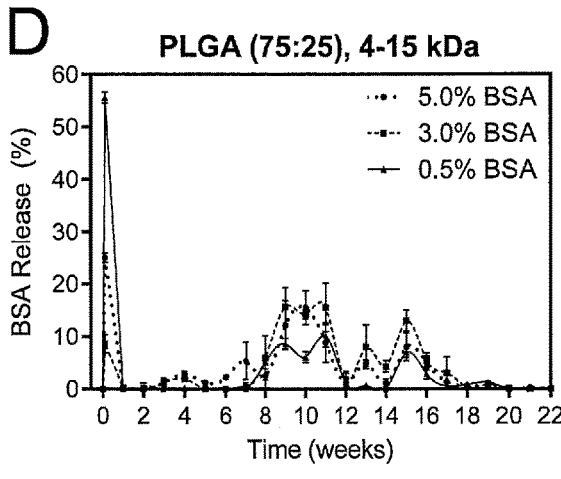

FIG. 21D is a graph of the release of bovine serum albumin over time (weeks) for 5% BSA, 3% BSA, and 0.5% BSA from PLGA (50:50), 9.5 kD, derivatized with a carboxylic group.

These figures show release from the same polymer, but with different molecular weights. This difference alone dramatically changed release profiles.

Figure 3A:
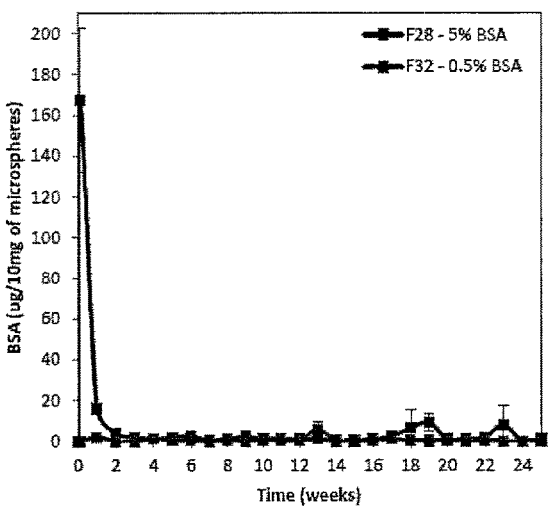
FIGS. 3A and 3B are graphs of the release of a model protein, bovine serum albumin ("BSA") (FIG. 3A, micrograms/10 mg of microspheres.
Figure 3B:
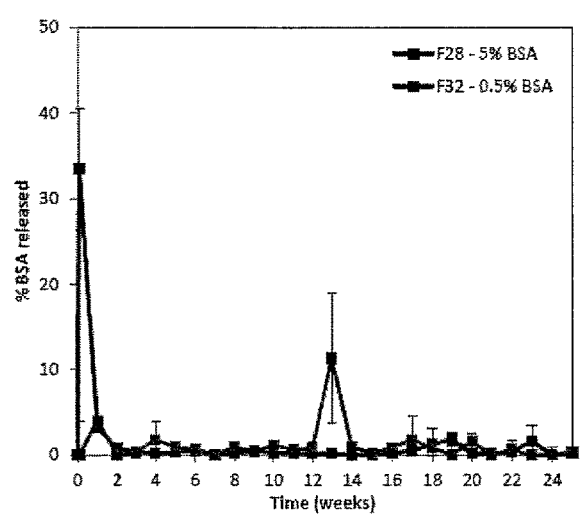

FIGS. 3A and 3B are graphs of the release of bovine serum albumin over time (weeks) for 5% BSA and 0.5% BSA from PLLA, 50 kD.

Figures 4A, 4B:
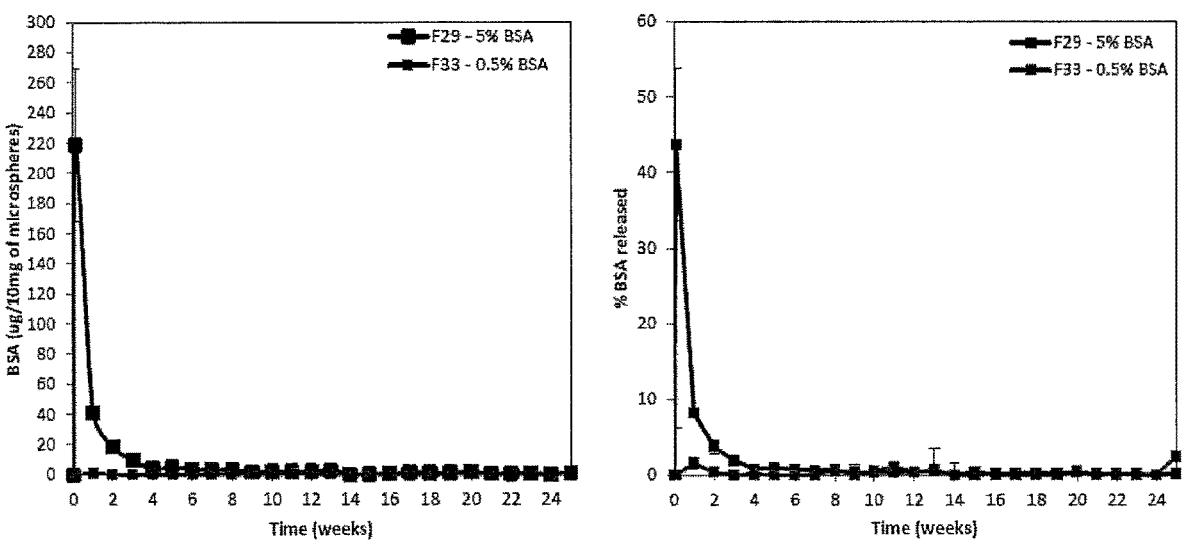
FIGS. 4A and 4B are graphs of the release of a model protein, bovine serum albumin ("BSA") (FIG. 4A, micrograms/10 mg of microspheres.

FIGS. 4A and 4B are graphs of the release of bovine serum albumin over time (weeks) for 5% BSA and 0.5% BSA from PLLA, 100 kD.

Figure 5A:
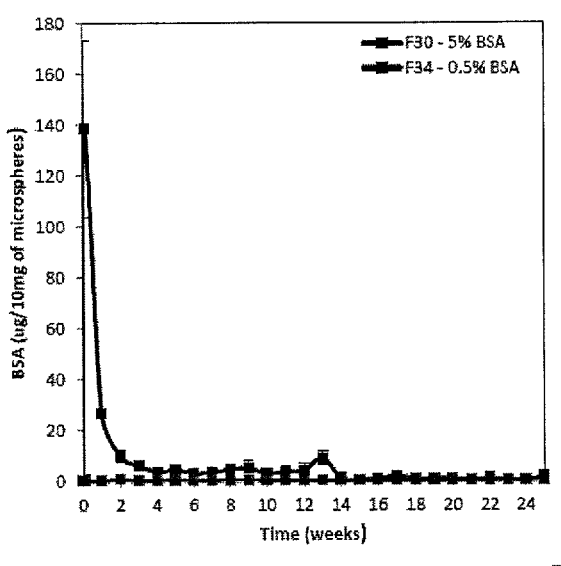
FIGS. 5A and 5B are graphs of the release of a model protein, bovine serum albumin ("BSA") (FIG. 5A, micrograms/10 mg of microspheres.
Figure 5B:
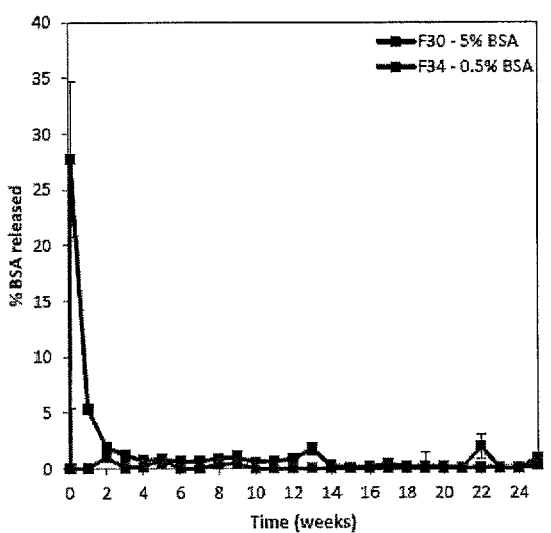

FIGS. 5A and 5B are graphs of the release of bovine serum albumin over time (weeks) for 5% BSA and 0.5% BSA from PLLA, 300 kD.

The only difference between these three graphs is the molecular weight. However, in no case were there substantial, distinct periods of release similar in scope to those in FIG. 21.

Figure 6A:
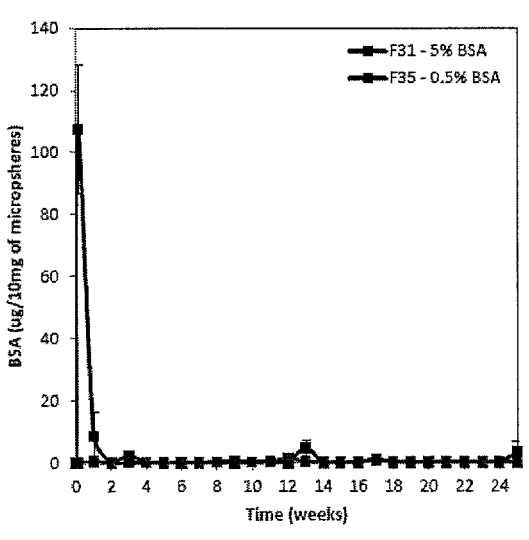
FIGS. 6A and 6B are graphs of the release of a model protein, bovine serum albumin ("BSA") (FIG. 6A, micrograms/10 mg of microspheres.
Figure 6B:
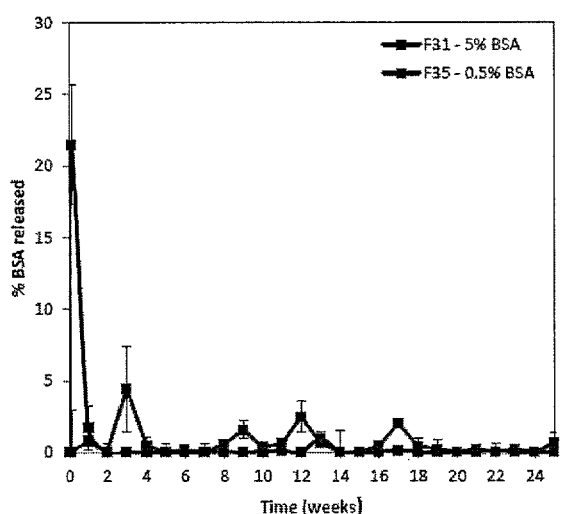

FIGS. 6A and 6B are graphs of the release of bovine serum albumin over time (weeks) for 5% BSA and 0.5% BSA from P(d,l)LA, 20 kD. The results are similar to FIGS. 3-5 and 21.

The best results were obtained using PLGA-COOH (50: 50). This is summarized in FIGS. 7A and 7B for PLGA formulations (FIG. 7A) compared to bolus injections (FIG. 7B).

The details of the formulations used for FIG. 7A are presented in Table 3 (see also Tables 4 and 5). In Table 3, the difference between F3 and F7 is the Mw of the polymer. F5 has high loading of BSA. Note that F3 and F7 have about 3 equivalent doses, while F5 has a large initial dose followed by two smaller ones—this is very similar to an initial bolus with 2 booster shots. Formulations are injected into animals on day 0 (single injection), while bolus controls are injected 3 times during the course of the study to mimic formulation release kinetics. Negative controls include blank microspheres for formulations and saline for bolus injections. Injection volumes were 200 μl (max volume for subcutaneous (SC) injection in mice). Two injections of 200 μl injection, one per leg, were performed Maximum injectable microsphere concentration was 50 mg/ml.

TABLE 3

Amount of BSA released (μg) at first, second and third peaks following injection of F3, F5 and F7 formulations.

| Groups (n = 10) | Amount of BSA (μg) | | | |
| | $1^{st}$ peak | $2^{nd}$ peak | $3^{rd}$ peak | Total |
|---|---|---|---|---|
| F3: 0.5% BSA, 20 k BI-502H, 50/50 | 22.2 | 19.8 | 21.6 | 63.6 |
| F7: 0.5% BSA, 31 k PLGA, 50/50 | 23.0 | 13.6 | 34.0 | 70.6 |
| Bolus control (2) | 22.0 | 22.0 | 22.0 | 66.0 |
| F5: 5% BSA, 31 k PLGA, 50/50 | 298.0 | 68.4 | 65.4 | 431.8 |
| Bolus control (1) | 298.0 | 68.4 | 65.4 | 431.8 |

Figure 8A:
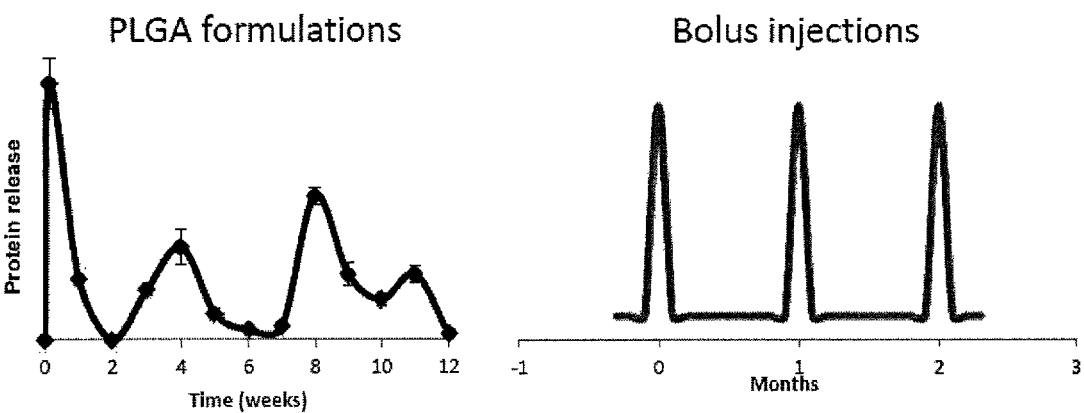
FIGS. 8A and 8B are graphs of the release of 0.5% of a model protein, bovine serum albumin ("BSA") compared to release of 0.5% of another model protein ovalbumin ("OVA") (FIG. 8A, micrograms/10 mg of microspheres.
Figure 8B:
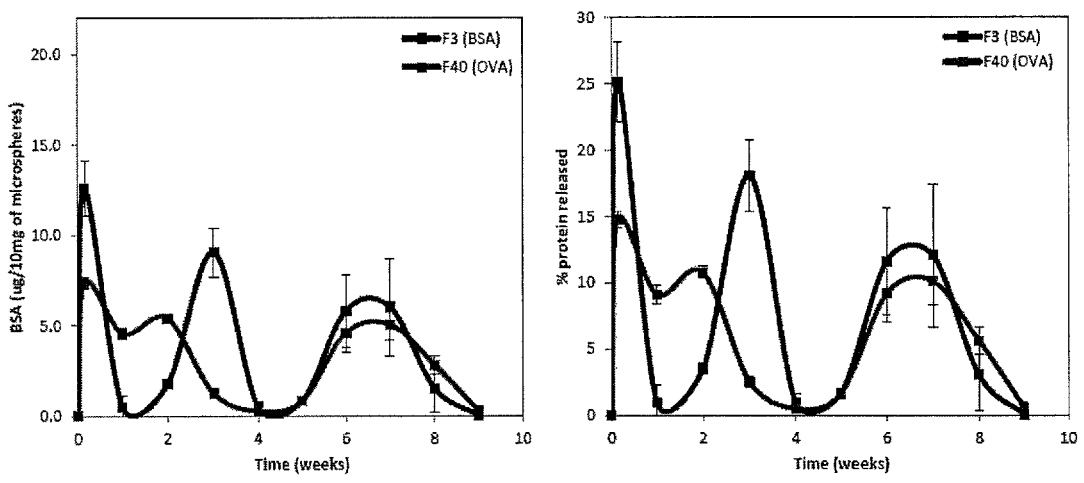

FIGS. 8A and 8B are graphs of the release of 0.5% of bovine serum albumin compared to release of 0.5% of ovalbumin over time (weeks) from PLGA (50:50), 20 kD, derivatized with a carboxylic group.

Figures 9A, 9B:
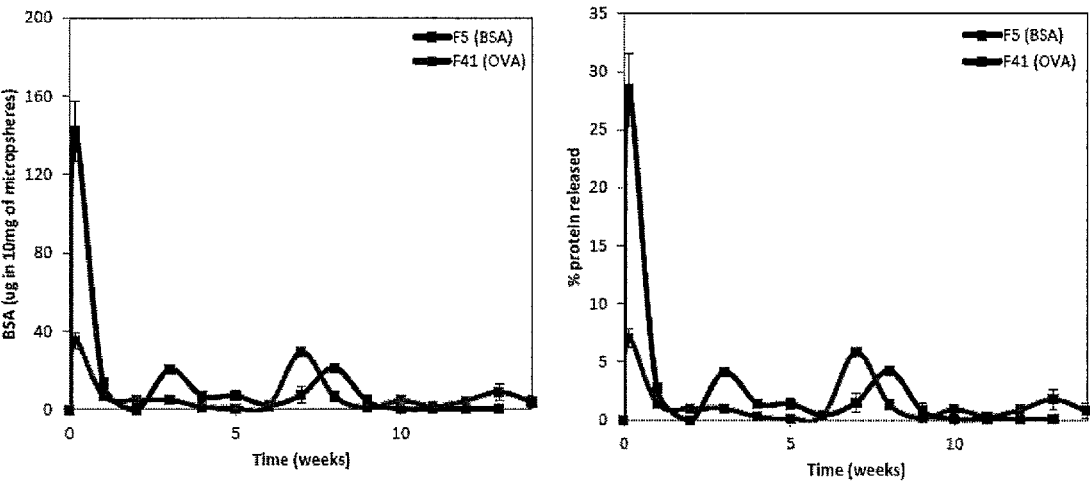
FIGS. 9A and 9B are graphs of the release of 5% of a model protein, bovine serum albumin ("BSA") compared to release of 5% of another model protein ovalbumin ("OVA") (FIG. 9A, micrograms/10 mg of microspheres.

FIGS. 9A and 9B are graphs of the release of 5% of bovine serum albumin compared to release of 5% of ovalbumin over time (weeks) from PLGA (50:50), 31 kD, derivatized with a carboxylic group.

Figure 10A:
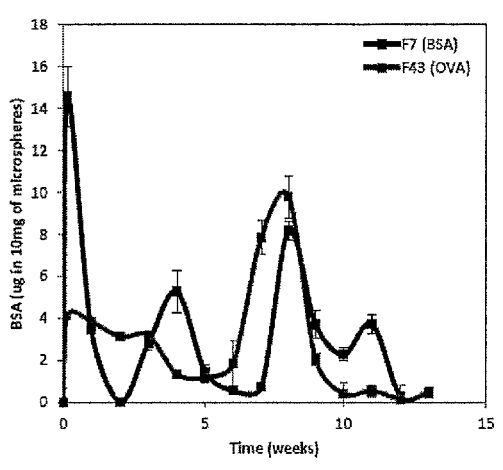
FIGS. 10A and 10B are graphs of the release of 0.5% of a model protein, bovine serum albumin ("BSA") compared to release of 0.5% of another model protein ovalbumin ("OVA") (FIG. 10A, micrograms/10 mg of microspheres.
Figure 10B:
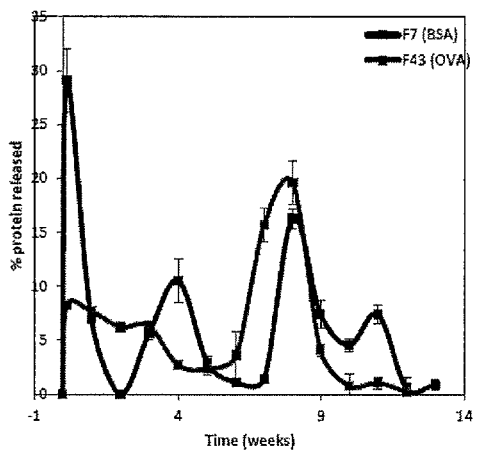

FIGS. 10A and 10B are graphs of the release of 0.5% of bovine serum albumin compared to release of 0.5% of ovalbumin over time (weeks) from PLGA (50:50), 31 kD, derivatized with a carboxylic group.

These all shows excellent results, varying only due to the molecular weights of the polymers or the percent loading.

Example 2: Predicted Release Profiles from
Microparticles Made by Emulsion Compared to
Microparticles Made by 3DP Particles fabricated by computer-controlled inkjet 3D-printing can be made with identical micrometer-scale dimensions, drug loadings, and spatial locations of drugs within the polymer microstructures. The main difference between the two methods is that emulsion based particles (left) are matrix based and the drug is homogeneously distributed throughout the particle. The 3D or micromolded particle is shown on the right. The vaccine and polymer are distinctly separated, where the vaccine is in the core and the polymer is only in the shell. These distinctions allow for unique control of release kinetics between the two particle types. Also, the micromolded/3D printed particle allows for higher loadings since the core size can also be controlled.

The release graph of FIG. 11C is based on the data in Example 1.

In the schematic of FIG. 11E, the drug or the vaccine is encapsulated in polymer microspheres and dispersed throughout the polymer matrix (A). Once hydrated, any drug on the surface is immediately released (B) thus causing the initial burst. Following this event, the microspheres have remnant pores through which drug can slowly diffuse causing the secondary burst (C). Finally, when the polymer bulk erodes, due to significant Mw degradation, the reminder of the drug is released in a third burst (D).

Example 3: Selection of Parameters for
Piezoelectric Jetting to Make Microparticles Materials and Methods Optimization:
    Correct the applied pressures from the nozzles (wave-
        form) to jet out uniform, single droplets of PLGA
    Optimize viscosity of the PLGA solution (Z number)
    Low enough viscosity to jet out efficiently from the nozzle
    High enough viscosity to solidify on the substrate
    Studies have shown that proper drop formation in piezo-
electric drop-on-demand (DOD) ink-jet printing can be
described using the dimensionless Z number. The Z number
is determined by the ink's fluid properties (surface tension,
density, and viscosity) and the size of a printhead's nozzle.
    Z number ranges can be defined for determining ink
printability with a specific waveform.
    Characterize PLGA solutions using the Z number:
    Solvents are chosen based on PLGA solubility and physi-
        cal properties (i.e. vapor pressure and boiling point).
    Once an optimal waveform is determined for one PLGA
        solution ink, that same waveform can be used to print
        with different MW PLGAs, by using PLGA solutions
        that have Z numbers within a certain range.
Results
    The waveform for jetting BSA and IPV solutions was
optimized as shown in FIG. 13. This allows filling of the
polymer printer particles with vaccine.

Example 4: Studies to Minimize Loss of IPV
D-Antigen and Increase Stability During
Lyophilization and Encapsulation Studies were conducted to optimize methods and reagents
for concentrating IPV prior to encapsulation, to prevent loss
of D-antigen due to lyophilization. Methods that can be used
include centrifugal filters and dialysis.
    Excipients that may reduce D-antigen loss during emul-
sion process were tested. BSA has been used with some
success. The current studies utilized sugars. Varying sugar
concentrations for forming sugar glass was tested. Varying
humidity conditions for drying was also tested.
    Comparisons with other solvent systems for the sponta-
neous emulsion process were also made. In the initial
studies, chloroform/acetone was used for the organic phase.
In subsequent studies, ethyl acetate was used as a substitute
for dichloromethane (DCM).

Materials and Methods

Figure 14A:
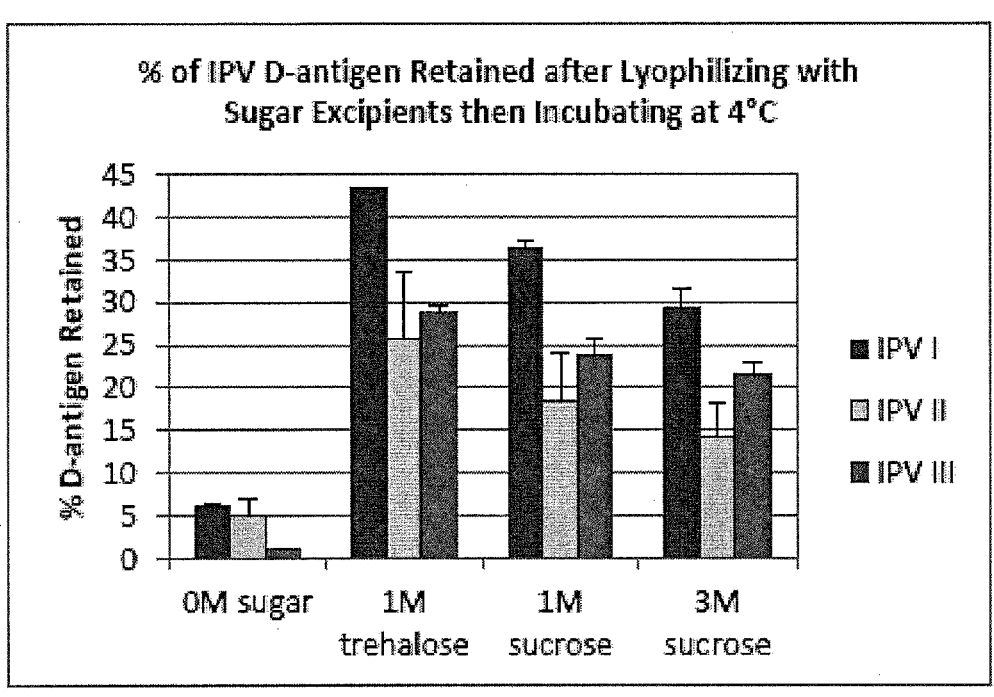
FIGS. 14A-14C are graphs of the percent D-antigen (IPV type I, II, and III) retained after lyophilizing with sugar excipients 1 M trehalose, 1 M sucrose, and 3 M sucrose, then incubating at 4° C., 25° C. or 37° C.
Figure 14B:
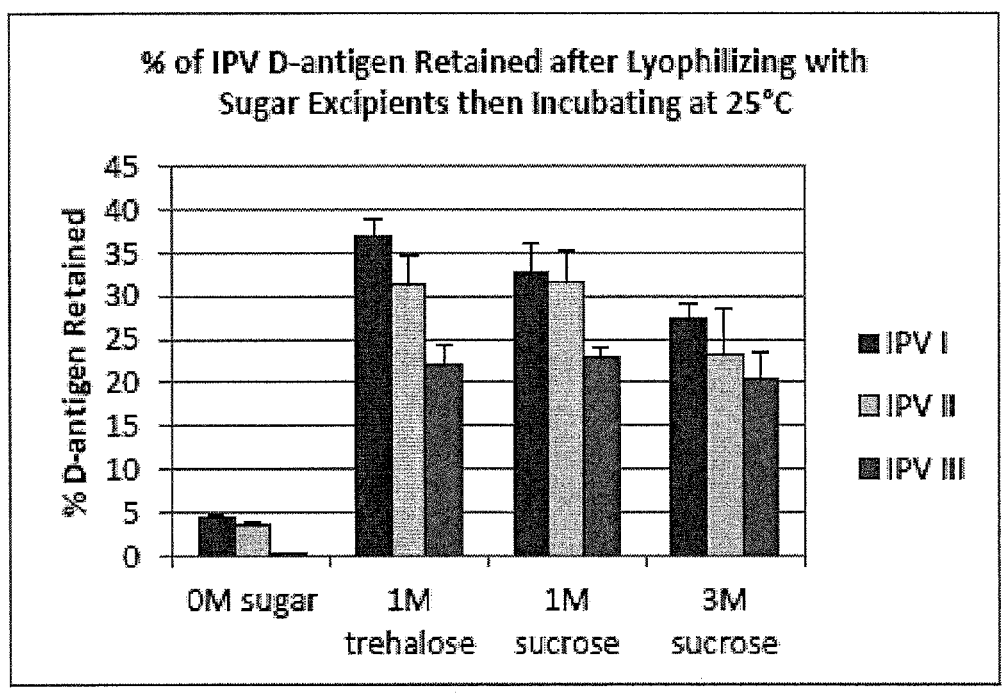
Figure 14C:
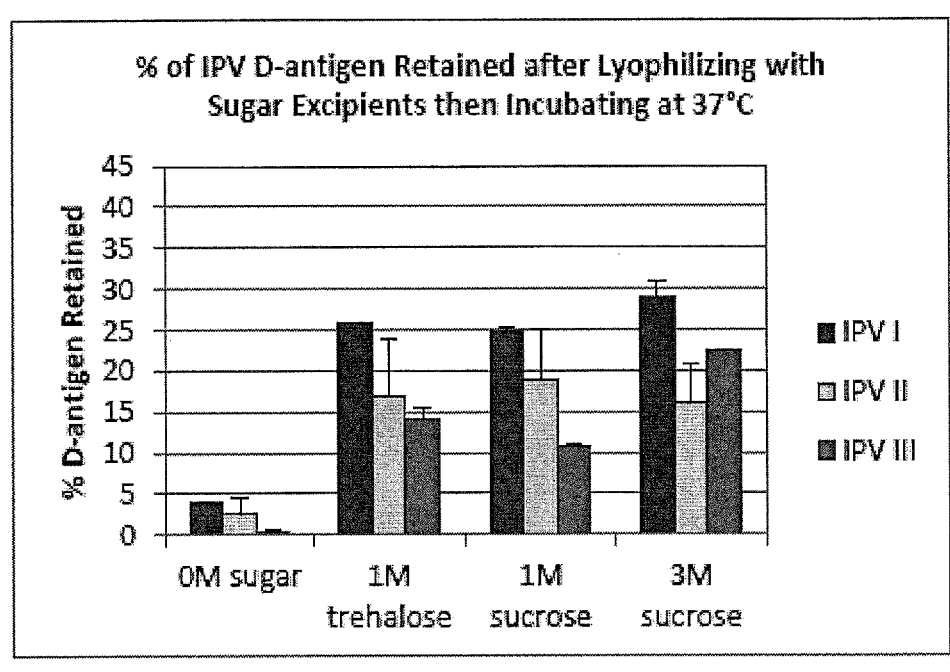

Alcock et al. reported that viruses incorporated into sugar
glass display long-term solid-state stability. (Alcock et al.,
*Science Translational Medicine,* 2(19):19-19ra12 (2010))
IPV stability in 3D-printed substrates was tested in a similar
manner. IPV solutions containing co-dissolved sugars (su-
crose and trehalose) were deposited onto a scaled-up PLA
structure printed using the MakerBot Replicator 2. Drying of
the IPV/sugar solutions was done at ambient humidity
(~20% humidity), which was higher than that used by
Alcock et al. (~10%).
Results
    FIGS. 14A, 14B and 14C are graphs of the percent
D-antigen (IPV type I, II, and III) retained after lyophilizing
with sugar excipients 1 M trehalose, 1 M sucrose, and 3 M
sucrose, then incubating at 4° C., 25° C. or 37° C.

Figure 15A:
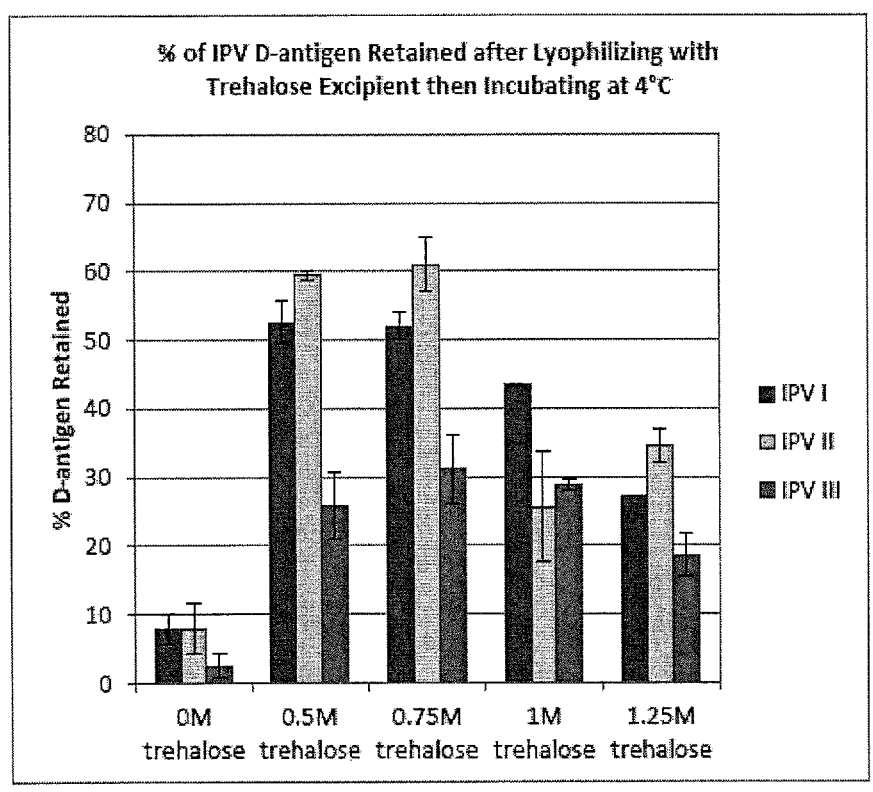
FIGS. 15A and 15B are graphs of the percent D-antigen (IPV type I, II, and III) retained after lyophilizing with 0, 0.5, 0.75, 1 or 1.25 M trehalose, 1 then incubating at 4° C.
Figure 15B:
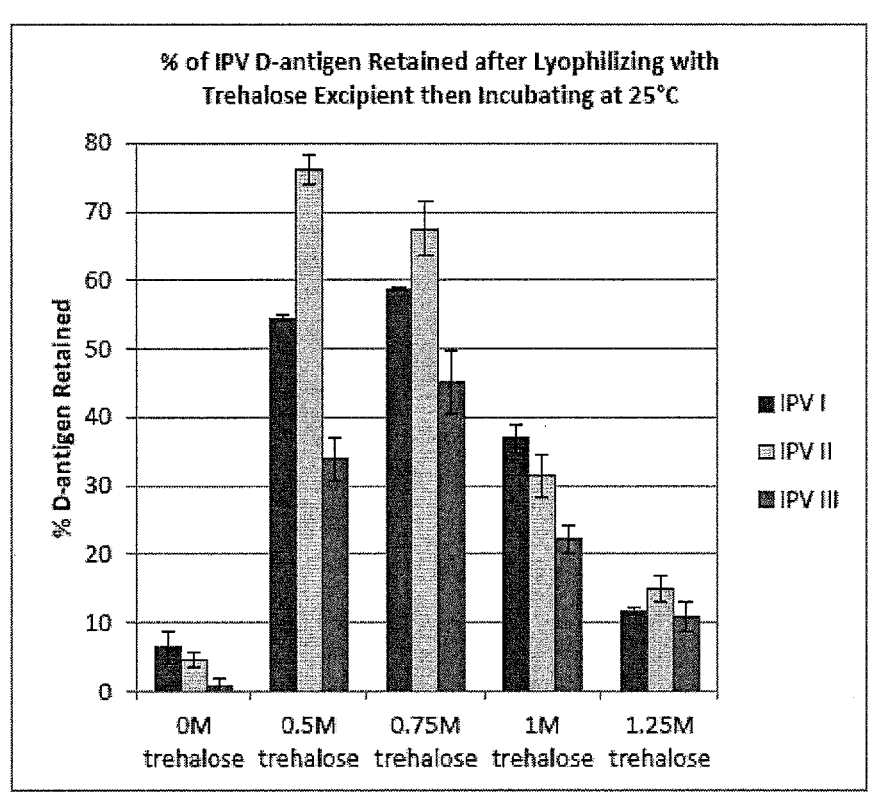
Figure 16A:
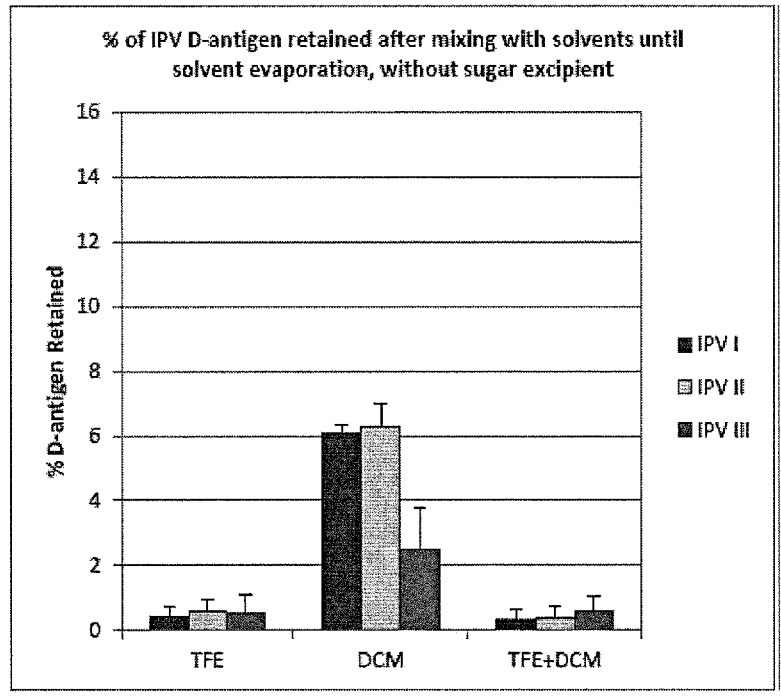
FIGS. 16A and 16B are graphs of the percent D-antigen (IPV type I, II, and III) retained after mixing with solvents until solvent evaporation, with solvents tetrafluoroethylene ("TFE"), dichloromethane ("DCM"), or TFE and DCM, without sugar excipient (FIG. 16A) or with 0.75 M trehalose as excipient (FIG. 16B).
Figure 16B:
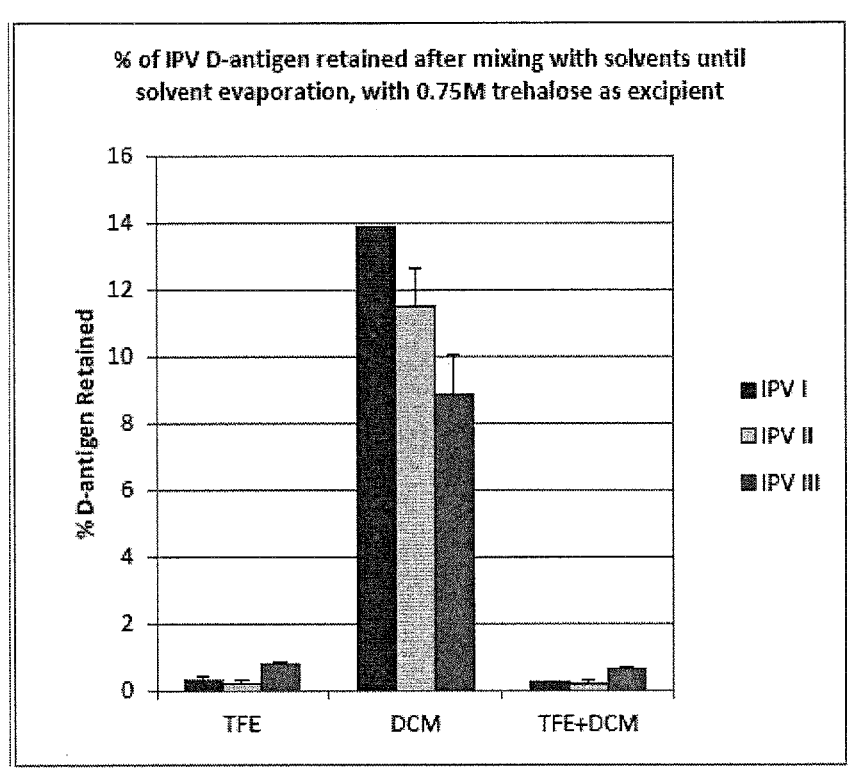
Figure 17A:
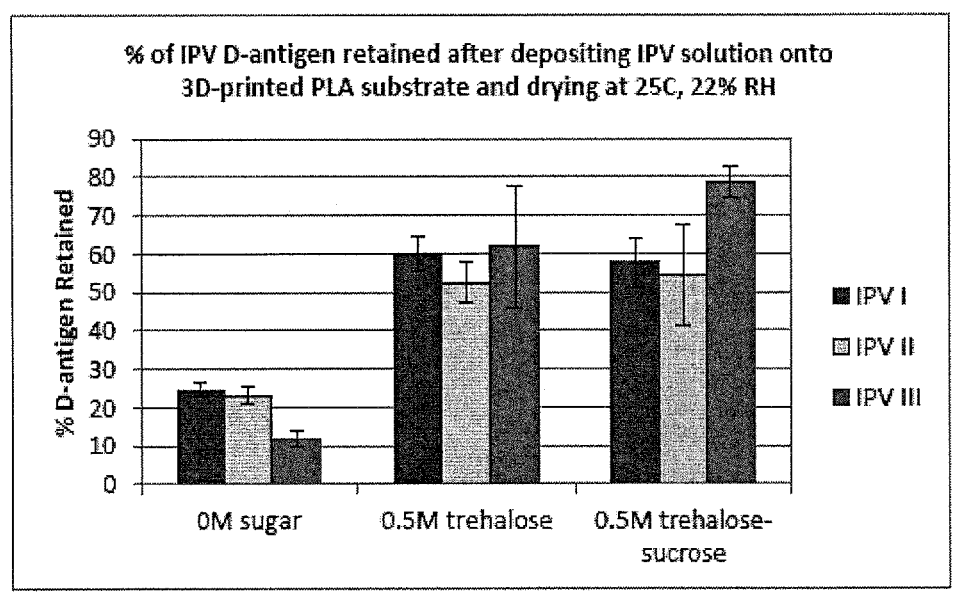
FIG. 17A is a graph of the percent D-antigen (IPV type I, II, and III) retained after IVP with 0 M sugar, 0.5 M trehalose, or 0.5 M trehalose-sucrose is printed onto 3D-printed PLA substrate and dried at 25° C., 22% RH.
Figure 17B:
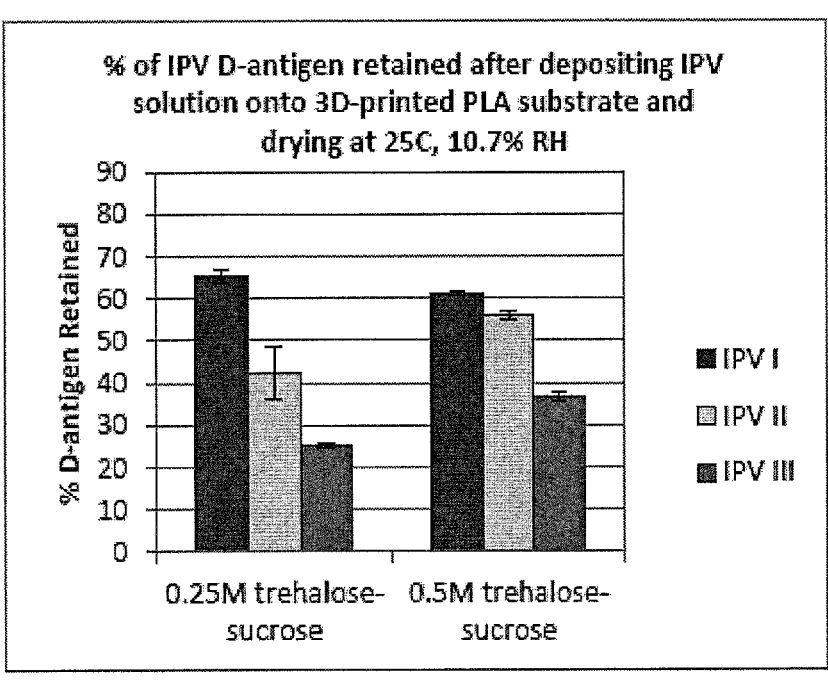
FIG. 17B is a graph of the percent D-antigen (IPV type I, II, and III) retained after IVP with 0.25 M trehalose or 0.5 M trehalose-sucrose is printed onto 3D-printed PLA substrate and dried at 25° C., 10.7% RH.
Figure 18A:
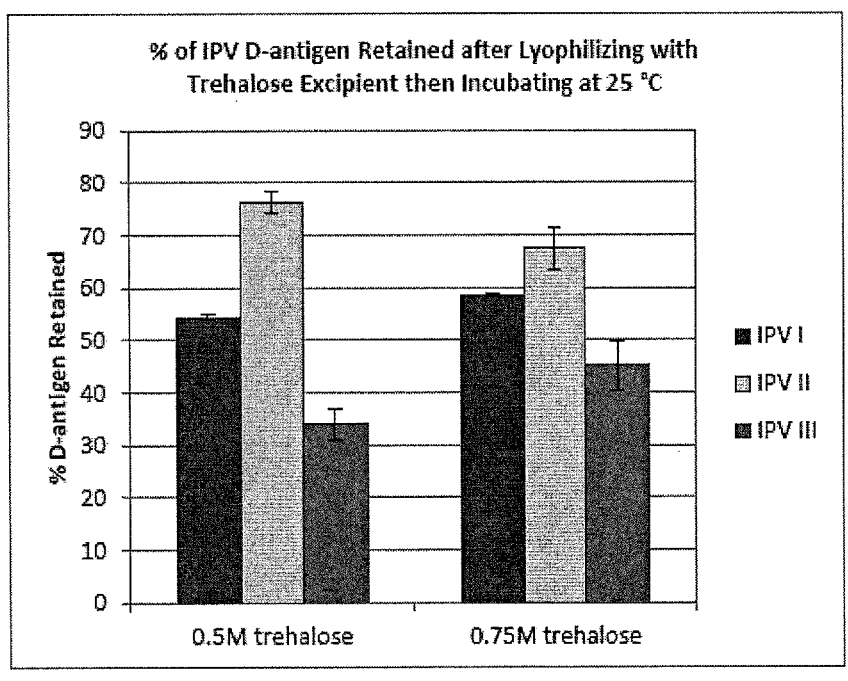
FIGS. 18A and 18B are graphs of the percent D-antigen retained after lyophilization with 0.5 or 0.75 M trehalose then incubating with 25° C.
Figure 18B:
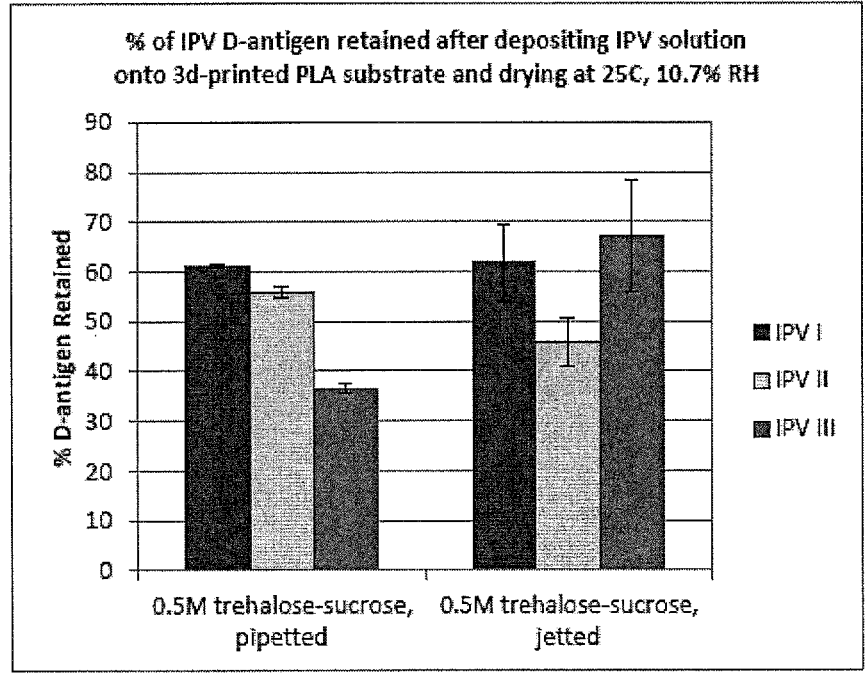

The results demonstrate that the sugar significantly
increased the stability of the IPV, and that there were few
differences between stability at 4° C. and 25° C., while
stability was less at 37° C. The results also showed that the
stability is different depending on the IPV type.
    FIGS. 15A and 15B are graphs of the percent D-antigen
(IPV type I, II, and III) retained after lyophilizing with 0,
0.5, 0.75, 1 or 1.25 M trehalose, 1 then incubating at 4° C.
(FIG. 15A) or 25° C. (FIG. 15B). The best results were
obtained with 0.5 M and 0.75 M trehalose.
    FIGS. 16A and 16B are graphs of the percent D-antigen
(IPV type I, II, and III) retained after mixing with solvents
until solvent evaporation, with solvents tetrafluoroethylene
("TFE"), dichloromethane ("DCM"), or TFE and DCM,
without sugar excipient (FIG. 16A) or with 0.75 M trehalose
as excipient (FIG. 16B). DCM was statistically significantly
better. IPV was not stable when exposed to the organic
solvents during the encapsulation process, even when treha-
lose was used as an excipient.
    FIG. 17A is a graph of the percent D-antigen (IPV type I,
II, and III) retained after IVP with 0 M sugar, 0.5 M
trehalose, or 0.5 M trehalose-sucrose is printed onto
3D-printed PLA substrate and dried at 25° C., 22% RH. FIG.
17B is a graph of the percent D-antigen (IPV type I, II, and
III) retained after IVP with 0.25 M trehalose or 0.5 M
trehalose-sucrose is printed onto 3D-printed PLA substrate
and dried at 25° C., 10.7% RH.
    Alcock et al. allowed virus/sugar solution to dry onto
substrate under controlled conditions (20-25° C., 2-10%
RH). Drying for FIG. 17A involved IPV/sugar solutions on
PLA substrates within a ventilated cell culture hood (20-25°
C., 22.9% RH). Drying for FIG. 17B involved IPV/sugar
solutions on PLA substrates in a desiccator (20-25° C.,
10.7% RH). Stability was better for room temperature/
humidity (all three IPV types had>50% D-antigen retained).
    FIGS. 18A and 18B are graphs of the percent D-antigen
retained after lyophilization with 0.5 or 0.75 M trehalose
then incubating with 25° C. (FIG. 18A) or after lyophiliza-
tion with 0.5 M trehalose-sucrose, pipetted, or 0.5 M treha-
lose-sucrose, jetted, then drying at 25° C., 10.7% RH (FIG.
18B).
    These studies demonstrate that the best results were
obtained by storing the 3D-printed PLA particles containing
lyophilized IPV at room temperature and humidity (~20%
relative humidity) The studies also demonstrated that jetting
the IPV, rather than lyophilizing the IPV, did not signifi-
cantly decrease IPV stability.

Figure 19A:
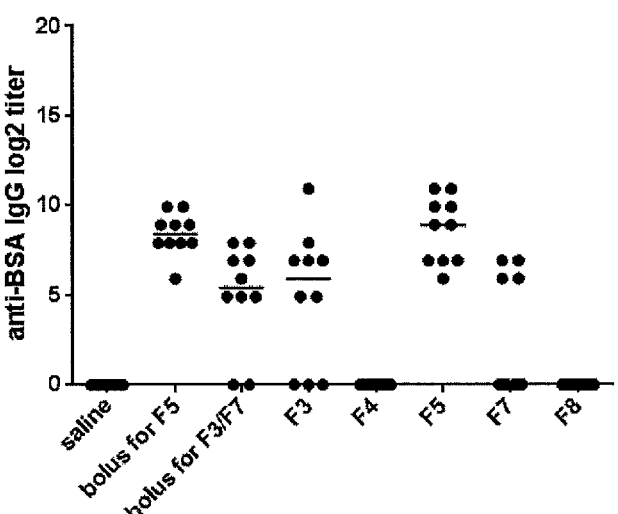
Figure 19B:
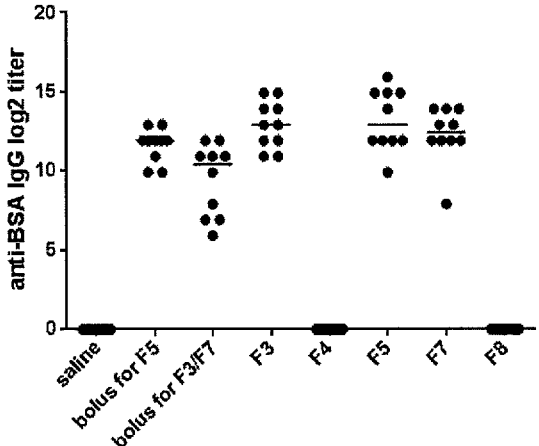

Example 5: Short-Term In Vivo Immunogenicity of
BSA-Containing PLGA Formulations The immune response, presented as the anti-BSA IgG
(antibody) titer, was measured at 1, 2, and 4 weeks following
injection of formulations F3, F5 and F7, presented in Table
3 above and Table 4 below. Formulations F4 and F8 are
blank microspheres (no drug), used as negative controls (see
Table 4).
    The results are presented in FIGS. 19A, 19B, and 19C.
The antibody titer (log 2) is plotted for the various groups at
1, 2, and 4 weeks. The negative controls are all zero and the
microsphere formulations are generating an equivalent or
stronger response compared to the bolus control.

Example 6: Long-Term In Vivo Immunogenicity of BSA-Containing PLGA Microspheres

Materials and Methods

Materials

Poly(D,L-lactic-co-glycolic acid) (PLGA Resomer® RG 502 H, RG 503 H, RG 504 H, and RG 752 H) and BSA were purchased from Sigma-Aldrich (St. Louis, MO). Poly(vinyl alcohol) (PVA, Mw=25,000) was purchased from Polysciences, Inc. (Warrington, PA). Dichloromethane (DCM) and 2,2,2-trifluoroethanol (TFE) used in this study were reagent grade.

Microsphere Fabrication

Sixteen formulations of PLGA microspheres containing BSA (Table 4) were fabricated using a spontaneous single-emulsion method (Fu et al., *J Pharm Sci,* 92:1582-1591, 2003; and Jaklenec et al., *Biomaterials,* 29:185-192, 2008). Briefly, 200 mg of PLGA were dissolved in 10 mL of 4:1 DCM:TFE and mixed with 300 μL of BSA in water. Mixing formed a clear, single-phase solution that was then added to 200 mL of 5% (w/v) PVA in water. The emulsion formed spontaneously and was stirred at room temperature for 3 hours. Particles were then collected via centrifugation, washed five times with water, and lyophilized. When prepared for in vivo use, organic phase and BSA solutions were filtered through 0.2 μm polytetrafluoroethylene filters (Whatman, Little Chalfont, England) and combined in a sterile laminar flow hood.

Microsphere Characterization

Microsphere size distribution was determined using a Multisizer 3 Coulter Counter. Histograms were created using a bin size of 0.39 μm and smoothed using central moving average with a window size of ±5 bins. Scanning electron microscope (SEM) images were collected using a JSM-5600LV SEM (JEOL, Tokyo, Japan) at an acceleration voltage of 5 kV. Prior to imaging, samples were coated with Au/Pd using a Hummer 6.2 Sputtering System (Anatech, Battle Creek, MI) to prevent surface charging.

TABLE 4

Microsphere formulations and size characterization.

| Formulation | BSA (% w/w) | PLGA M_w (kDa) | PLGA Ratio | Particle Size (μm) | 90% of Particles Below (μm) |
|---|---|---|---|---|---|
| A (F1) | 5 | 7-17 | 50:50 | 10.5 ± 6.8 | 18.5 |
| B (F2) | 3 | 7-17 | 50:50 | 10.6 ± 6.4 | 18.1 |
| C (F3) | 0.5 | 7-17 | 50:50 | 10.3 ± 6.2 | 22.1 |
| D (F4) | 0 | 7-17 | 50:50 | 10.5 ± 5.9 | 17.4 |
| E (F5) | 5 | 24-38 | 50:50 | 8.6 ± 6.7 | 21.4 |
| F (F6) | 3 | 24-38 | 50:50 | 11.4 ± 8.3 | 21.4 |
| G (F7) | 0.5 | 24-38 | 50:50 | 12.1 ± 8.2 | 23.1 |
| H (F8) | 0 | 24-38 | 50:50 | 11.4 ± 7.2 | 20.2 |
| I (F9) | 5 | 38-54 | 50:50 | 14.1 ± 9.4 | 25.4 |
| J (F10) | 3 | 38-54 | 50:50 | 12.0 ± 7.1 | 20.3 |
| K (F11) | 0.5 | 38-54 | 50:50 | 11.9 ± 6.8 | 20.6 |
| L (F12) | 0 | 38-54 | 50:50 | 11.9 ± 6.4 | 19.7 |
| M (F13) | 5 | 4-15 | 75:25 | 11.3 ± 7.0 | 19.7 |
| N (F14) | 3 | 4-15 | 75:25 | 12.2 ± 7.4 | 21.2 |
| O (F15) | 0.5 | 4-15 | 75:25 | 12.4 ± 7.5 | 21.1 |
| P (F16) | 0 | 4-15 | 75:25 | 11.7 ± 6.5 | 19.9 |

In Vitro BSA Release

Ten milligrams of microspheres were dispersed into 1 mL phosphate-buffered saline (PBS) in capped tubes and incubated on a rotating platform at 37° C. At each time point (1 day, then weekly for 1-13 weeks), samples were centrifuged at 1500 relative centrifugal force (RCF) for 5 min, after which the supernatant was collected. Samples were then resuspended in fresh PBS and returned to the incubator for sampling at subsequent time points. BSA release from microspheres was quantified using a bicinchoninic acid (BCA) assay and normalized to the total amount released by the end of the study. Samples were run in triplicate and data reported as mean±standard deviation.

In Vivo Administration of BSA Microspheres

All animal work was approved by MIT's Committee on Animal Care. Briefly, female BALB/c mice between 6 and 8 weeks of age received injections of (1) BSA-loaded microspheres, (2) unloaded microspheres, (3) bolus BSA, or (4) saline-only. While mice in the first two groups received only one injection, those receiving a bolus BSA or saline-only were injected again at 4 and 8 weeks to match the amount and timing of BSA release from PLGA microspheres in vitro. Samples were dissolved or suspended (when applicable) in 200 μl of saline and injected subcutaneously into each hind limb for a total of 400 μl. Table 5 contains the exact dosing regimen for each group. At week 0, 1, 2, 4, 6, 8, and 10, 100 μl of blood was sampled sub-mandibularly and, after clotting, was centrifuged at 2000 RCF for 10 minutes at 4° C. to separate the serum.

Immunogenicity of BSA Release from PLGA Microspheres

Serum antibody titers against BSA were determined using an endpoint enzyme-linked immunosorbent assay (ELISA). 96-well Maxisorp ELISA plates (Thermo Fisher Scientific, Waltham, MA) were coated overnight at 4° C. with 100 μL of a 100 μg/ml solution of BSA in 0.1M sodium bicarbonate. Plates were then washed three times in PBS containing 0.05% Tween 20 (PBST) and then incubated in 5% non-fat milk in PBST for 2 hours at 37° C. as a blocking agent. Following another series of three washes with PBST, mouse serum samples were added in four-fold serial dilutions and incubated for 2 hours at 37° C. The extent of serum dilution increased as the study progressed and titers rose. Plates were then washed five times with PBST and incubated at 37° C. with horseradish peroxidase-conjugated goat anti-mouse secondary antibody (Southern Biotechnology Associates, Birmingham, Alabama) diluted 1:1000 in blocking buffer for 2 hours. Plates were washed an additional five times with PBST and developed using 100 μL of p-nitrophenyl phosphate solution prepared from tablets dissolved in 1× diethanolamine buffer from an alkaline phosphate substrate kit (Bio-Rad, Hercules, CA). After 10 minutes, the reaction was stopped by adding 100 μL of 0.4M sodium hydroxide to each well and absorbance values were read at 405 nm using a Tecan Infinite M200 Pro microplate reader (Männedorf, Switzerland). Titers were reported as the reciprocal of the highest serum dilution that yielded an absorbance greater than 2-fold above background values.

TABLE 5

Dosing regimen for in vivo BSA administration.

| Group | Amount of BSA (μg) | | | |
|---|---|---|---|---|
| | First Dose | Second Dose | Third Dose | Total |
| Formulation C (0.5% BSA, 7-17 kDa PLGA)* | 22 | 20 | 22 | 64 |
| Formulation G (0.5% BSA, 24-38 kDa PLGA)* | 23 | 14 | 34 | 71 |
| Low Dose Bolus BSA | 22 | 22 | 22 | 66 |
| Formulation E (5% BSA, 24-38 kDa PLGA)* | 298 | 68 | 65 | 431 |

TABLE 5-continued

Dosing regimen for in vivo BSA administration.

| Group | Amount of BSA (µg) | | | |
| | First Dose | Second Dose | Third Dose | Total |
|---|---|---|---|---|
| High Dose Bolus BSA | 298 | 68 | 65 | 431 |
| Unloaded PLGA microspheres, 7-17 kDa | 0 | 0 | 0 | 0 |
| Unloaded PLGA microspheres, 24-38 kDa | 0 | 0 | 0 | 0 |
| Saline | 0 | 0 | 0 | 0 |

All PLGA used in vivo was 50:50.
*Indicates theoretical dose based on in vitro results.

Statistical Analysis

All data in Table 4 and FIG. 20 are reported as mean±standard deviation. In vitro studies were performed in experimental triplicate while in vivo studies were performed with ten experimental replicates for all groups at all time points, except Formulation C at week 10 in which nine replicates were used due to insufficient blood volume from one animal. Time-matched antibody titers were compared using one-way ANOVA statistical analysis for the three low dose groups and Student's unpaired two-tailed t-test for comparing the high dose microspheres and bolus injections. Comparisons of peak antibody titers were performed using Student's unpaired two-tailed t-test with the Holm-Bonferroni correction at a significance level of 0.05 to counteract the effect of multiple comparisons.

Results

Characterization of BSA-Containing PLGA Microspheres

All sixteen formulations of PLGA and BSA produced spherical microparticles with broad distributions of particle sizes (Table 4). The size and shape of Formulations C, G, and E, which were used for in vivo studies, were representative of all formulations. Formulation C produced microspheres that were 10.3±6.2 µm in diameter yet because of the cubic relationship between volume and diameter, particles smaller than 10.3 µm contained just 4.2% of the antigen load assuming homogeneous distribution of BSA in PLGA (Narasimhan et al., J Control Release, 47:13-20, 1997). Larger particles contained a majority of the antigen with 90% of the volume contained in particles larger than 22.1 µm for Formulation C. Formulations G and E demonstrated similar characteristics with particle diameters of 12.1±8.2 and 8.6±6.7 µm respectively, yet with 90% of particle volume contained in particles larger than 23.1 and 21.4 µm respectively. Histograms of microsphere diameter and volume distribution can be seen in FIG. 20A-20F. Particles at the large end of the distribution also contributed substantially to surface area effects as 50% of the cumulative particle surface area was present on particles larger than 23.67, 29.54, and 27.58 µm in diameter for Formulations C, G, and E respectively.

In Vitro Release of BSA from PLGA Microspheres

In vitro release kinetics from PLGA microspheres were determined by BCA assay and expressed as a percentage of the total BSA released during the duration of the experiment. BSA release and particle degradation occurred more quickly in PLGA microspheres fabricated using any of the three polymers with 50:50 ratios of lactic-to-glycolic acid compared to a 75:25 ratio. All microsphere formulations produced using PLGA with a 50:50 ratio degraded within 14 weeks whereas 75:25 PLGA degraded in 22 weeks. The timing of BSA release appeared to be more dependent on polymer type than BSA loading, though loading had a major effect on the size of the bursts in most cases. Low molecular weight (7-17 kDa) PLGA released in three distinct bursts over the course of 8 weeks and completely degraded by week 14 as seen in FIG. 21A. The medium molecular weight (24-38 kDa) PLGA also displayed three bursts spread over 9-12 weeks depending on BSA loading and degraded by week 14 (FIG. 21B). The highest molecular weight (38-54 kDa) PLGA released BSA over 9-12 weeks with prominent bursts at day 1 and week 8, but with more continuous release kinetics in between from the 3 and 5% BSA loaded microspheres (FIG. 21C). Microspheres made from low molecular weight (4-15 kDa) PLGA with a higher lactic acid content (75:25) degraded over 22 weeks and showed gradual semi-continuous release after an initial burst (FIG. 21D).

Out of the sixteen in vitro formulations, Formulations C, G, and E were chosen for the subsequent in vivo study based on their in vitro release kinetics. Formulation C microspheres were made using low molecular weight PLGA (7-17 kDa) loaded with 0.5% BSA, Formulation G with slightly higher molecular weight PLGA (24-38 kDa) and 0.5% BSA, and Formulation E with the same molecular weight PLGA as Formulation G, but with higher (5%) BSA loading. BSA release from Formulation C was characterized by three distinct peaks at day 1 when 33.4±5.1% of total BSA was released, at week 4 when 27.2±4.3% was released, and across the week 6 and week 7 time points during which 32.1±5.2% was released respectively (FIG. 21A). Minimal BSA release was observed at weeks 1, 2, 4, and 5, or after week 7 and microspheres were completely degraded by week 10 as evidenced by complete dissolution of the particles.

Formulation G microspheres were also characterized by BSA release in three bursts (FIG. 21B), but spread out over a longer timeframe. In addition, total microsphere degradation was observed after 14 weeks rather than 10 weeks for Formulation C. The first BSA burst from Formulation G was observed at the 1-day time-point, releasing 28.0±5.7% of total BSA. This was followed by a second burst of 12.9±2.9% at week 4, and an elongated burst at weeks 8 through 11 during which a cumulative 43.8±2.0% of BSA was released. Little-to-no BSA was observed in the release media at any other time points through complete degradation of the particles.

Formulation E microspheres released 63.7±7.3% of its BSA at day 1 which was the largest initial burst in terms of both total quantity and percentage of any of the formulations (FIG. 21C). The only time points with substantial BSA release following this initial burst were weeks 3 and 8 when 8.9±0.9% and 8.8±2.1% of the total load was released respectively. Similar to Formulation G, which used PLGA at the same molecular weight (24-38 kDa), Formulation E degraded completely at 14 weeks.

Immunogenicity of BSA-Containing PLGA Microspheres

The humoral immune response to each microsphere formulation was compared with a positive control consisting of three bolus injections matching the quantity and timing of BSA released from particles in vitro. Within experimental groups, a statistically significant increase in titer between consecutive weeks was used as evidence of release (one-sample paired t-test). Formulation C induced a significant increase in antibody titer compared to the previous time point at weeks 1, 2, and 4 (p<0.05, p<0.0001, and p<0.001 respectively), then decreased significantly at weeks 6 and 8 (p<0.01 and p<0.05 respectively), before stabilizing at week 10 (FIG. 22). Similarly, mice receiving Formulation G showed a significant increase in titer at weeks 1, 2, and 4

(p<0.05, p<0.001, and p<0.01 respectively), remained steady at week 6, and then fell significantly by week 8 (p<0.05) before stabilizing again at week 10. Formulation E induced a similar response as antibody titers increased significantly at weeks 1, 2, and 4 (p<0.001 for all), leveled off at week 6, and then decreased through the end of the study (p<0.05). Overall, the immune response to all three microparticle formulations demonstrated a similar progression over time as titers rose over the first 4 weeks then slowly decreased through week 10 (FIG. 22). However, the magnitude of antibody titers appeared highly dependent on BSA loading. Based on in vitro experiments, Formulation E released approximately 13 times more BSA than Formulations C at the earliest time point (1 day) due to a large initial burst and induced antibody titers that was 13-fold higher as well. This trend was also observed at the end of the study as the antibody titer induced by Formulation E was 8-fold higher than those associated with Formulation C after releasing 7 times as much BSA.

Antibody titers from animals receiving any of the BSA-loaded microsphere formulations were significantly higher than those from animals receiving dose-matched bolus injections after 2 and 4 weeks (p<0.05 and p<0.01 respectively). However, after boosting with a second bolus injection at week 4, titers were statistically similar between formulations and their dose-matched bolus group at 6 and 8 weeks. Then at week 10, following administration of the third bolus, animals receiving bolus BSA showed another spike in titer resulting in significantly higher antibody titers compared to all dose-matched microsphere groups at that time point (p<0.001).

While time-matched antibody titers suggest the timing of antigen presentation, peak antibody titers may be more useful indicators of immune response in this case due to a possible mismatch in the timing of antigen presentation (Paryani et al., *J. Pediatr,* 105:200-205 (1984); Barraclough et al., *Am J Kidney Dis,* 54:95-103 (2009)). The bolus injection schedule was chosen to match the timing of microsphere bursts in vitro, but accelerated in vivo degradation could have resulted in an offset in antigen release. As a result, at the end of the experiment antibody titers in the microsphere groups had been falling for weeks as would be expected in the absence of antigen, whereas titers in the bolus control groups reached their highest levels following the third injection. Comparing peak antibody titers helps to control for the effects of timing and determine which treatment was more immunogenic.

Antibody titers for Formulations C, G, and E peaked at 13.9±1.3, 13.7±2.2, and 16.1±2.1 on a log 2 scale respectively 4 weeks after microsphere administration, whereas the small and large dose-matched boluses peaked after 10 weeks at 15.5±1.5 and 17.7±0.8 log 2 titer respectively (FIG. 23). Formulations C and G (FIG. 23A) induced peak antibody titers that were not statistically different (p*=0.0645 and p*=0.0543 respectively) than the dose-matched bolus control consisting of three 22 μg BSA injections, using the Holm-Bonferroni correction method that has been recommended for multi-group titer comparisons (Reverberi, *Blood Transfus.* 6:37-45 (2008)). Formulation E (FIG. 23B) also induced peak titers that were not statistically different (p*=0.0784) than the dose-matched bolus control consisting of three bolus injections (Table 5).

Example 7: PLGA Micromolded Particles for Drug Delivery Materials and Methods Development of single drug particles involves three major steps: 1) shell microfabrication, 2) vaccine/drug filling and 3) particle sealing.

The shell microfabrication may use mask fabrication (lithography), fluoro-mold fabrication (UV core) and heat pressing of PLGA (120° C. for 30 min). The step of drug filling may be carried out by the Biodot robot, filling the core with 1.5 nL volume of the drug. The sealing is achieved by placing a PLGA cap on the shell and then sealing the particles at 37° C. for 5 min and acetone vapor for 5 min.

The schematic of the process is presented in FIGS. 12A-12D and 24A-24C. These microparticles may be manufactured as stacks, sealing each one with another at 37° C. for 5 min.

Results

The micromolded particle shells have an x, y, and z dimensions of 450×450×300 μm with a core of 100×100×100 μm (cap dimensions are 450×450×150 μm), or 200×200×150 μm, with a core of 100×100×100 μm. These dimensions allow the particles to be delivered with a 21 gauge needle (inner diameter 514 μm) or with a 23 gauge needle (inner diameter 337 μm).

Example 8. Single PLA Particles for Depositing Drug/Sugar Solution

Materials and Methods

IPV in 0.5 M trehalose and 0.5 M sucrose solution was deposited onto PLA particles then dried in the stem cell culture hood at room temperature. PLA particles may be 3D-printed using a Makerbot printer.

Results

Single PLA particles may serve as a useful platform for drying onto and delivering drugs and antigens, as this method allows to deposit drug or antigen in a sugar solution onto a substrate such that the drug or antigen is stabilized within a sugar glass. Studies on the stability of IPV antigens on PLA particles are presented in Examples below.

Example 9: Stability of the IPV Microspheres

The process of IPV microsphere formation presented in Example 1 above holds challenges for IPV stability during the manufacturing process. These challenges with a summary of the findings that overcome the challenges are presented in Table 6.

TABLE 6

Summary of obstacles to IPV stability, approaches taken to overcome the obstacles and findings.

| Obstacle | Approach | Findings |
|---|---|---|
| IPV is not stable in organic solvents or at organic/aqueous interface | Double emulsion method keeps IPV in an aqueous "bubble." Minimal direct contact with organics Co-encapsulate IPV with BSA or mild surfactant to reduce IPV exposure to | Double emulsionis effective Vortexing and sonication parameters can be tuned to maximize IPV recovery Excipients improve recovery |

TABLE 6-continued

Summary of obstacles to IPV stability, approaches taken to overcome the obstacles and findings.

| Obstacle | Approach | Findings |
|---|---|---|
| IPV may not survive the physical mixing processes that form the emulsion | aqueous/organic interface during emulsification<br>Use lower-energy mixing: homogenization, vortexing, low-amplitude sonication, etc. | Gelatin<br>Tween (polysorbate) 80 |
| IPV is not stable after drying | Change drying method (lyophilization, air-drying, vacuum)<br><br>Add excipients during drying<br><br>Co-encapsulate with excipients | Microspheres dried at room temp for 1 hr undervacuum show high IPV recovery<br>Sorbitol/MSG/MgCl$_2$ improves recovery during drying<br>Sorbitol/MSG/MgCl$_2$ can be co-encapsulated in w/o/o microspheres |
| IPV is not stable in microsphere matrix in hydrated, 37 C. environment | Co-encapsulate IPV with excipients to help maintain stability | Gelatin and sorbitol/MSG/MgCl$_2$ improve stability overtime |
| IPV is not stable in polymer degradation products | Co-encapsulate IPV with basic excipients to buffer acidic byproducts | IPV is not stable < pH 6 or > pH 8<br>Mg(OH)$_2$ buffers acidic byproducts |
| Microspheres do not show bursts of release at the desired time points | Change polymer composition (PLGA MW, ratio ofLA:GA)<br><br>Change excipients added to polymer | PLGAs of different MW and ratios are being tested with BSA microspheres<br>Microspheres containing pH-affecting additives are being tested |

Example 10: Co-Encapsulation of IPV with Gelatin or Mild Surfactant and Sonication Increase IPV Stability During Emulsification

Materials and Methods

Figure 25:
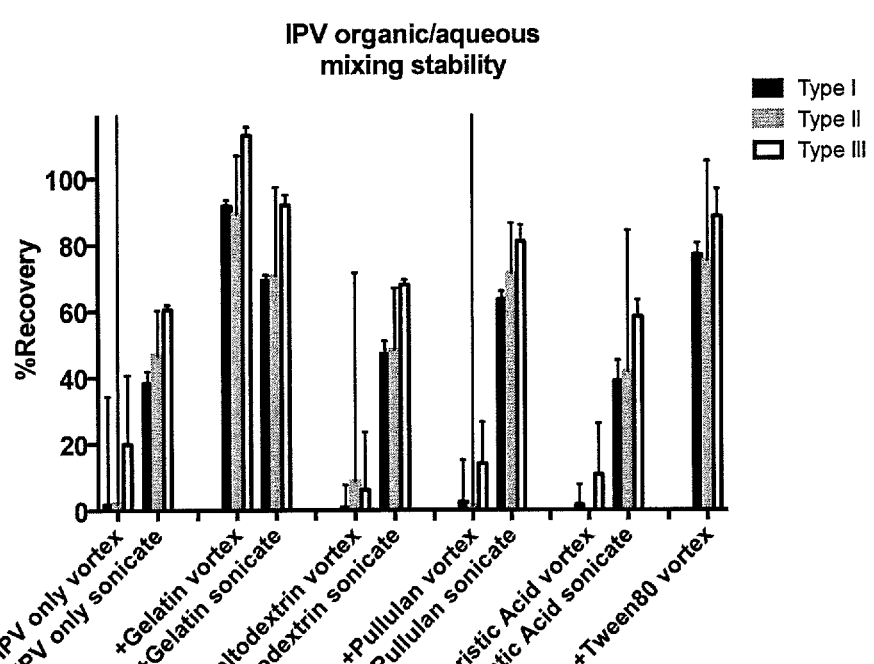
FIG. 25 is a bar graph showing the stability of IPV (% Recovery) with or without excipients gelatin, maltodextrin, pullulan, myristic acid, and Tween80, during organic/aqueous mixing by vortexing or sonication.

IPV was mixed with water and/or excipients at 100:1 w/w ratio. Excipients used were gelatin, maltodextrin, pullulan, myristic acid, and Tween80. IPV with excipients was then added to DCM, or PLGA/DCM. The mixture was vortexed for 10 sec on highest setting, or was sonicated 10 sec at 25% amplitude. ELISA buffer (1% BSA, 1% Triton-X 100 in PBS) was added, the mixture was vortexed for 10 sec on high setting, and layers were separated by centrifugation. The aqueous layer was removed and tested by ELISA.
Results Gelatin and Tween80 both improved the stability of type I, II and III IPV (FIG. 25).

Figure 26:
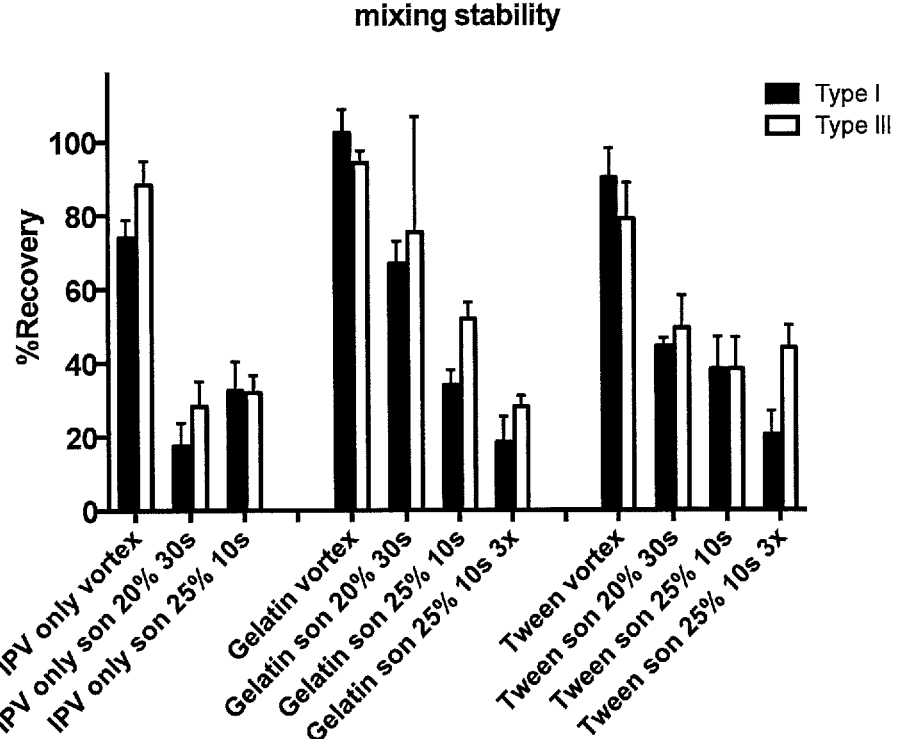
FIG. 26 is a bar graph showing the stability of IPV (% Recovery) with or without excipients gelatin, maltodextrin, pullulan, myristic acid, and Tween80, during organic/aqueous mixing with PLGA by vortexing or sonication (son=sonication).

Type I and III IPV, generally the most sensitive to damage, showed best recovery with sonication at 20% amplitude for 30 sec (FIG. 26).

Example 11: Drying of IPV and Excipients with Genevac Improves IPV Recovery

Materials and Methods

Figure 27:
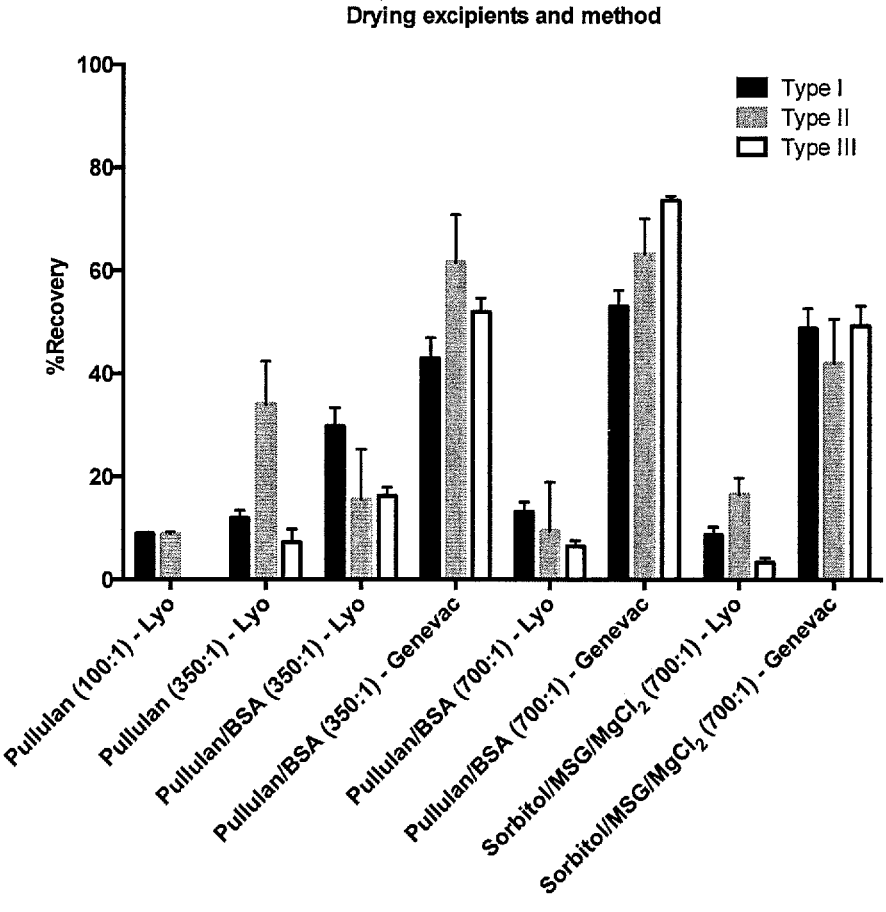
FIG. 27 is a bar graph showing the stability of IPV (% Recovery) with excipients pullulan, pullulan/BSA, sorbitol/MSG/MgCl2, following drying by overnight lyophylization, or using Genevac for 1 h at 30-35° C.

IPV was concentrated 26× and mixed with pullulan, pullulan/BSA, or sorbitol/MSG/MgCl2 at 100:1, 350:1, or 700:1 mass ratio. IPV with excipient was dried by lyophilization (overnight) or using Genevac (1 hr, 30-35° C.). Recovery was tested by ELISA after resuspending the dried IPV with excipients.
Results In all paired groups of lyophylization (Lyo) and Genevac (FIG. 27), Genevac showed higher recovery than lyophilization.

Example 12: Lyophilized IPV Shows Long-Term Stability at 37° C.

Materials and Methods

Figure 2:
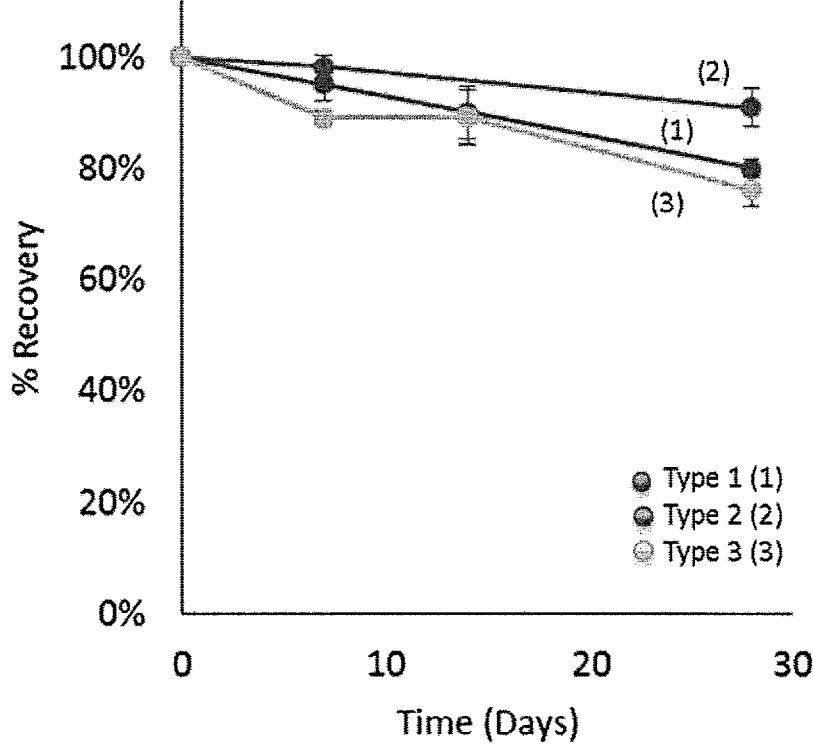
FIG. 2 is a line graph showing long-term stability of lyophilized IPV (type I, type II, and type III) with excipients at 37° C. in humidified atmosphere. The stability is expressed as percent recover (% Recovery) over time (days). On the line graph, the line for type I IPV is designated (1), the line for type II IPV is designated (2), and the line for type III IPV is designated (3).

IPV was mixed with excipients 10% sorbitol, 8.5% MSG, and 8.5% MgCl$_2$ at 40,000:1, and lyophilized in plastic tube. The lyophilized IPV with excipients was stored in a plastic tube in a pouch with desiccant at humidified atmosphere and 37° C. for up to 30 days. At various time points, the lyophilized IPV was resuspended and tested for recovery by ELISA.
Results Types I, II and III IPV in lyophilized form with excipients showed long-term stability when stored at 37° C. (FIG. 2).

Example 13: Changes in pH of Release Medium by PLGA Particles

Figure 29:
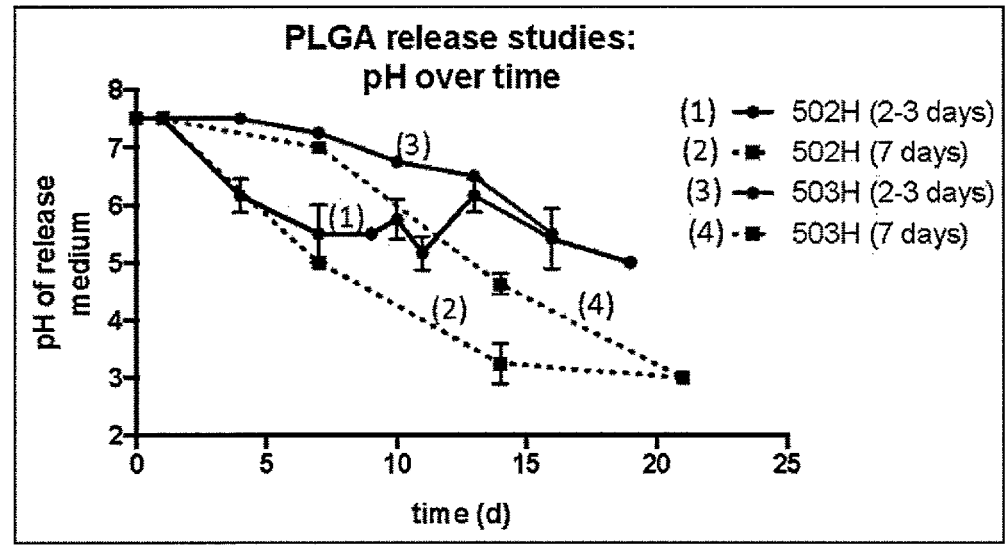
FIG. 29 is a line graph showing change in pH of release medium by PLGA particles over time (days). The line for PLGA 502H tested after replacing buffer every 2-3 days is designated (1), the line for PLGA 502H tested after replacing buffer every 7 days is designated (2), the line for PLGA 503H tested after replacing buffer every 2-3 days is designated (3), and the line for PLGA 503H tested after replacing buffer every 7 days is designated (4).

PLGA degrades by bulk erosion leading to acid buildup inside microspheres. During in vitro storage, finite volume of buffer may cause acid build up in tubes, which may lead to particle erosion and acid build up inside the microspheres. In in vivo applications, the buffer in local environment is constantly replenished with minimal acid build up outside of the particles. Because PLGA degrades by bulk erosion, acid build up inside the microspheres may be a problem. Therefore, several PLGA molecules were tested for changes in the pH of the release medium over time, when the buffer was changed every 2-3 days, or every 7 days.
Results Results in FIG. 29 demonstrate that PLGA molecules alone change the pH of the release medium making it more acidic over time. Although change of buffer every 2-3 days helps ameliorates this effect, it does not solve the problem.

Example 14. Excipients to Buffer the Acidic Products of PLGA Microspheres

It was observed that Type I IPV was relatively stable at pH 7.4 at 37° C., and type II and type III IPV were stable at pH 6-8 at 37° C. Therefore, several excipients were tested for their buffering capacity to buffer the acidic products of PLGA microspheres.

Materials and Methods

Figure 28:
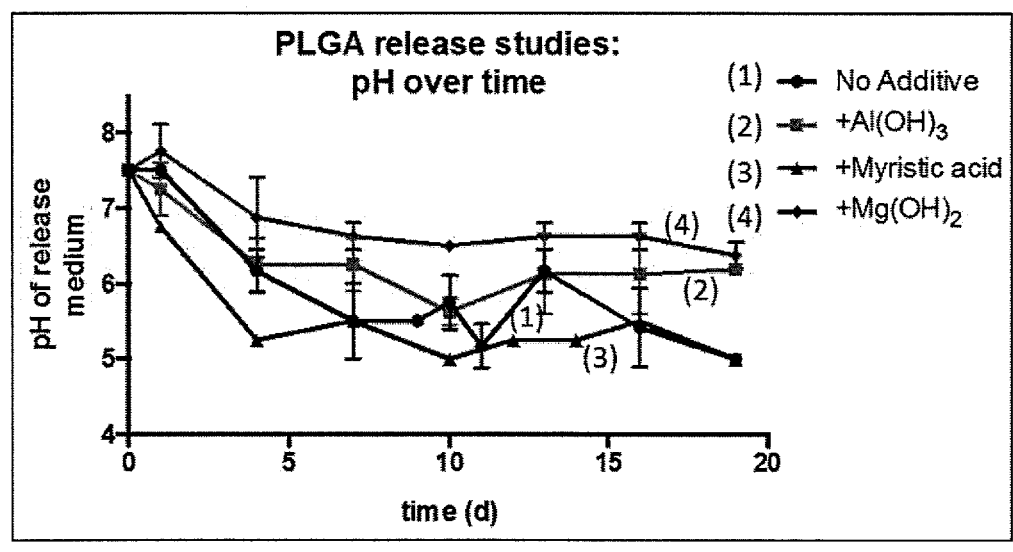
FIG. 28 is a line graph showing change in pH of release medium by PLGA particles over time (days) in the presence of buffering agents $Al(OH)_3$ (line (2)), myristic acid (line (3)), and $Mg(OH)_2$ (line (4)). The line representing change in pH of release medium over time in the absence of buffering agents is labeled (1).

Buffering agents, such as $Mg(OH)_2$, $Al(OH)_3$, and myristic acid, were incorporated into PLGA microspheres to minimize changes in pH of release medium. Also, $Mg(OH)_2$ has little to no solubility in water, it remains distributed throughout the polymer matrix and can potentially buffer the internal compartment. $Al(OH)_3$ is a known adjuvant and can increase immunogenicity Results The results in FIG. 28 demonstrate that $Mg(OH)_2$ was able to buffer acidic byproducts in the release medium and stabilize the pH of the release medium at about pH 7.

Example 15. IPV Microspheres Incorporating Stabilizing Excipients

Based on the investigations of Examples 9-14, PLGA microspheres incorporating IPV and various stabilizing additives were generated. These formulations are presented in Table 7 below, and were made with PLGA 502H. Other formulations with higher MW polymers, like PLGA 503H, are also contemplated.

Example 16. IPV Stability after Drying on PLA Allows Use of Lower Excipient:Vaccine Ratios D-antigen retention after drying 26X Trivalent IPV on PLA for 16 hours at room temperature and humidity was tested. Excipient used was 10% sorbitol, 8.5% MSG, 8.5% $MgCl_2$. The ratios of excipient to vaccine tested were 300 to 1, 100 to 1, 60 to 1, 30 to 1, or no excipient. The percent of D-antigen retained was assayed by ELISA.

Results

Upon drying of the solutions on PLA, no significant drop in stability was observed when going down to a 30:1 ratio (FIG. 1). This data indicated that concentrated excipient-free IPV could be dried on PLA cubes without much loss of antigen activity.

Example 17. Other Formulations of Concentrated IPV Mixed with Excipients and Dried in a PLA Cube The formulations listed in Table 8 represent % D-antigen retained when concentrated IPV was mixed with indicated excipient solutions (columns "Polyol" and "Other") at the indicated ratios (column "Excip:Vax," all indicated ratios are 100:1) and dried in PLA cubes overnight.

Unless defined otherwise, all technical and scientific terms used herein have the same meanings as commonly understood by one of skill in the art to which the disclosed invention belongs. Publications cited herein and the materials for which they are cited are specifically incorporated by reference. Those skilled in the art will recognize, or be able to ascertain using no more than routine experimentation, many equivalents to the specific embodiments of the invention described herein. Such equivalents are intended to be encompassed by the following claims.

TABLE 7

| | | | | | | | |
|---|---|---|---|---|---|---|---|
| IPV microsphere formulations incorporating stabilizing additives for polymer degradation-based bursts of drug/antigen release. S/M/M refers to 10% sorbitol, 8.5% MSG, 8.5% $MgCl_2$ | | | | | | | |
| mg polymer (MW) | Approx. DUIPV loaded (Type I/Type II/Type III) | Additives to IPV phase | Additives to PLGA phase | Outer stirring phase (2$^{nd}$ emulsion) | Mixing (1$^{st}$ emulsion) | Mixing speed/time | Drying |
| 20 (12 k) | 216/62/187 | 4 mg gelatin | None | Oil: mineral oil + Span 80 | Sonicator | 20% amplitude, 30 sec | 22 mg S/M/M |
| 20 (12 k) | 216/62/187 | 4 mg gelatin | 10% myristic acid | Aqueous: 1% PVA, 5% sucrose | Sonicator | 20% amplitude, 30 sec | 22 mg S/M/M |
| 20 (12 k) | 216/62/187 | 4 mg gelatin | 10% $Al(OH)_3$ | Aqueous: 1% PVA, 5% sucrose | Sonicator | 20% amplitude, 30 sec | 22 mg S/M/M |
| 20 (12 k) | 216/62/187 | 8.65 mg S/M/M | None | Oil: mineral oil + Span 80 | Sonicator | 20% amplitude, 30 sec | No excipient |
| 20 (12 k) | 216/62/187 | 4 mg gelatin | 10% $Mg(OH)_2$ | Aqueous: 1% PVA, 5% sucrose | Sonicator | 20% amplitude, 30 sec | 22 mg S/M/M |
| 20 (12 k) | 216/62/187 | 2 mg gelatin 4.3 mg S/M/M | 10% $Mg(OH)_2$ | Oil: mineral oil + Span 80 | Sonicator | 20% amplitude, 30 sec | No excipient |
| 20 (12 k) | 216/62/187 | 4 mg gelatin | 10% $Mg(OH)_2$ | Oil: mineral oil + Span 80 | Sonicator | 20% amplitude, 30 sec | No excipient |
| 20 (31 k) | 216/62/187 | 4 mg gelatin | 10% $Mg(OH)_2$ | Oil: mineral oil + Span 80 | Sonicator | 20% amplitude, 30 sec | No excipient |
| 20 (31 k) | 216/62/187 | 2 mg gelatin 4.3 mg S/M/M | 10% $Mg(OH)_2$ | Oil: mineral oil + Span 80 | Sonicator | 20% amplitude, 30 sec | No excipient |
| 20 (12 k) | 216/62/187 | 4 mg gelatin | 10% $Mg(OH)_2$, 10% myristic acid | Oil: mineral oil + Span 80 | Sonicator | 20% amplitude, 30 sec | No excipient |

TABLE 7-continued

IPV microsphere formulations incorporating stabilizing additives for polymer degradation-based bursts of drug/antigen release. S/M/M refers to 10% sorbitol, 8.5% MSG, 8.5% MgCl$_2$

| mg polymer (MW) | Approx. DUIPV loaded (Type I/ Type II/Type III) | Additives to IPV phase | Additives to PLGA phase | Outer stirring phase ($2^{nd}$ emulsion) | Mixing ($1^{st}$ emulsion) | Mixing speed/time | Drying |
|---|---|---|---|---|---|---|---|
| 20 (12 k) | 216/62/187 | 4 mg gelatin | 5% Mg(OH)$_2$ 5% Al(OH)$_3$ | Oil: mineral oil + Span 80 | Sonicator | 20% amplitude, 30 sec | No excipient |

TABLE 8

Percent D-antigen (type 1, type 3, and type 3 IPV) retained on PLA particles after air-drying for one day with the indicated excipients and IPV at a ratio of 100:1.

| Polyol | Other | Excip:Vax | Days | ° C. | Drying | Storage | Type 1 | Type 2 | Type 3 |
|---|---|---|---|---|---|---|---|---|---|
| none | Silk | 100 | 1 | 25 | Air-dry | BSL cabinet | 4 | 18 | 4 |
| Maltodextrin | Arginine | 100 | 1 | 25 | Air-dry | BSL cabinet | 7 | 84 | 38 |
| Methyl Cellulose | Ectoines | 100 | 1 | 25 | Air-dry | BSL cabinet | 62 | 52 | 57 |
| HPMC | Ubiquitin | 100 | 1 | 25 | Air-dry | BSL cabinet | 59 | n/a | 79 |
| HPMC | MSG | 100 | 1 | 25 | Air-dry | BSL cabinet | 65 | n/a | 73 |
| none | Gelatin, ubiquitin | 100 | 1 | 25 | Air-dry | BSL cabinet | 75 | 74 | 79 |
| Sucrose | Gelatin | 100 | 1 | 25 | Air-dry | BSL cabinet | 77 | 78 | 79 |
| Ca Heptagluconate | k Phosphate | 100 | 1 | 25 | Air-dry | BSL cabinet | 78 | 80 | 86 |
| Trehalose | Threonine | 100 | 1 | 25 | Air-dry | BSL cabinet | 81 | 83 | 84 |
| CMC | Gelatin | 100 | 1 | 25 | Air-dry | BSL cabinet | 82 | 82 | 84 |
| Glycerol | MSG | 100 | 1 | 25 | Air-dry | BSL cabinet | 82 | 84 | 86 |
| Ca-Heptagluconate | Gelatin | 100 | 1 | 25 | Air-dry | BSL cabinet | 85 | n/a | 83 |
| Sorbitol | Peptone | 100 | 1 | 25 | Air-dry | BSL cabinet | 84 | 87 | 85 |
| Trehalose | Ubiquitin | 100 | 1 | 25 | Air-dry | BSL cabinet | 84 | 91 | 90 |
| Mannitol | Glutamine | 100 | 1 | 25 | Air-dry | BSL cabinet | 91 | n/a | 89 |
| Sorbitol | Glycine | 100 | 1 | 25 | Air-dry | BSL cabinet | 90 | 88 | 90 |
| Maltodextrin | Glutamine | 100 | 1 | 25 | Air-dry | BSL cabinet | 88 | n/a | 94 |
| Maltodextrin | None | 100 | 1 | 25 | Air-dry | BSL cabinet | 93 | 95 | 91 |
| Mannitol | Ectoines | 100 | 1 | 25 | Air-dry | BSL cabinet | 92 | 94 | 92 |
| Trehalose | Glycine | 100 | 1 | 25 | Air-dry | BSL cabinet | 93 | 90 | 92 |
| Sorbitol | Ectoines | 100 | 1 | 25 | Air-dry | BSL cabinet | 96 | n/a | 92 |
| Sucrose | Threonine | 100 | 1 | 25 | Air-dry | BSL cabinet | 95 | n/a | 97 |
| Sorbitol | MSG, MgCl2 | 100 | 1 | 25 | Air-dry | BSL cabinet | 99 | 95 | 99 |

We claim:

1. A microdevice for delivering a therapeutic or prophylactic agent to a human or animal, the microdevice comprising:
a non-spherical biocompatible polymeric shell defining a discrete region including the therapeutic or prophylactic agent; and
a biocompatible polymeric cap;
wherein the biocompatible polymeric cap and the biocompatible polymeric shell are sealed together,
wherein at least one dimension of the microdevice is between about 1 μm to about 1000 μm.

2. The microdevice of claim 1 wherein at least one of the polymeric shell and the polymeric cap comprises a water insoluble polymer.

3. The microdevice of claim 1 wherein at least one of the polymeric shell and the polymeric cap comprises polyester or polyanhydride.

4. The microdevice of claim 1 wherein at least one of the polymeric shell and the polymeric cap comprises poly(lactic acid), poly(glycolic acid), or poly(lactic-co-glycolic acid).

5. The microdevice of claim 1, wherein the polymeric shell, the polymeric cap, or both, are formed from micro-molding, three-dimensional printing, or nanoimprint lithography.

6. The microdevice of claim 1 wherein the therapeutic or prophylactic agent comprises an antigen.

7. A vaccine formulation comprising a plurality of the microdevices of claim 6, optionally wherein the formulation is configured to provide pulsatile release of the therapeutic or prophylactic agent, wherein the pulsatile release includes releasing the therapeutic or prophylactic agent at two or more time periods.

8. The microdevice of claim 1, wherein all dimensions of the microdevice are between about 1 μm to about 1000 μm.

9. The microdevice of claim 1, wherein at least one dimension of the microdevice is between about 100 μm to about 1000 μm.

\* \* \* \* \*